US008945586B2

(12) United States Patent
Moreno Igoa et al.

(10) Patent No.: US 8,945,586 B2
(45) Date of Patent: Feb. 3, 2015

(54) THERAPEUTIC USE OF THE ENCODING SEQUENCE OF THE CARBOXY-TERMINAL DOMAIN OF THE HEAVY CHAIN OF THE TETANUS TOXIN

(75) Inventors: María Moreno Igoa, Saragossa (ES); Ana Cristina Calvo Royo, Saragossa (ES); Maria Jesús Muñoz Gonzalvo, Saragossa (ES); Maria Pilar Zaragoza Fernández, Saragossa (ES); Rosario Osta Pinzolas, Saragossa (ES); José Aguilera Avila, Bellaterra (ES)

(73) Assignees: University of Zaragoza, Saragossa (ES); Autonomous University of Barcelona, Bellaterra (ES)

( * ) Notice: Subject to any disclaimer, the term of this patent is extended or adjusted under 35 U.S.C. 154(b) by 859 days.

(21) Appl. No.: 12/754,552

(22) Filed: Apr. 5, 2010

(65) Prior Publication Data

US 2010/0261656 A1 Oct. 14, 2010

Related U.S. Application Data

(63) Continuation-in-part of application No. PCT/ES2008/070186, filed on Oct. 3, 2008.

(30) Foreign Application Priority Data

Oct. 5, 2007 (ES) ................................ P200702621

(51) Int. Cl.
*A61K 39/08* (2006.01)
*C07K 14/33* (2006.01)
*A61K 38/48* (2006.01)

(52) U.S. Cl.
CPC ............ *C07K 14/33* (2013.01); *A61K 38/4886* (2013.01)
USPC ...................................... 424/239.1; 514/17.7

(58) Field of Classification Search
None
See application file for complete search history.

(56) References Cited

U.S. PATENT DOCUMENTS 4,479,940 A 10/1984 Bizzini

FOREIGN PATENT DOCUMENTS

| | | | |
|---|---|---|---|
| CA | 2 701 521 | A1 | 4/2009 |
| EP | 0 057 140 | B1 | 7/1985 |
| WO | WO 99/09057 | A2 | 2/1999 |
| WO | WO 2004/021992 | A2 | 3/2004 |
| WO | WO 2005/025592 | A2 | 3/2005 |
| WO | WO 2007/082973 | A1 | 7/2007 |
| WO | WO 2008/094583 | A2 | 8/2008 |
| WO | WO 2009/043963 | A1 | 4/2009 |

OTHER PUBLICATIONS

Jackowski, British Journal of Neurosurgery 9:303-317 (1995).*

Rudinger, In "Peptide Hormones" (ed. J.A. Parsons) Univeristy Park Press, Baltimore, pp. 1-7.*

Bordet, T., et al. "Neuronal Targeting of Cardiotrophin-1 by Coupling with Tetanus Toxin C Fragment," *Molecular and Cellular Neurosciences* 17(5): 842-854, Academic Press, United States (2001).

Brown. R.H. Jr., "Amyotrophic Lateral Sclerosis. Insights from Genetics," *Archives of Neurology* 54(10): 1246-1250, American Medical Assn., United States (1997).

Ciriza, J., et al., "A Genetic Fusion GDNF-C Fragment of Tetanus Toxin Prolongs Survival in a Symptomatic Mouse ALS Model," *Restorative Neurology and Neuroscience* 26(6): 459-465, IOS Press, Netherlands (2008).

Ciriza, J., et al., "Antiapototic Activity Maintenance of Brain Derived Neurotrophic Factor and the C Fragment of the Tetanus Toxin Fusion Protein." *Cent. Eur. J. Biol.* 3(2): 105-112, Versita, Poland (2008).

Francis, J.W., et al. "CuZn Superoxide Dismutase (SOD-1): Tetanus Toxin Fragment C Hybrid Protein for Targeted Delivery of SOD-1 to Neuronal Cells," *J. Biol. Chem.* 270(25): 15434-15442, American Society for Biochemistry and Molecular Biology, United States (1995).

Francis, J.W., et al., "Tetanus Toxin Fragment C as a Vector to Enhance Delivery of Proteins to the CNS," *Brain Res.* 1011(1): 7-13, Elsevier/North-Holland Biomedical Press, Netherlands (2004).

Gil, C., et al., "C-terminal Fragment of Tetanus Toxin Heavy Chain Activates Akt and MEK/ERK Signalling Pathways in a Trk Receptor-Dependent Manner in Cultured Cortical Neurons," *Biochem. J.* 373: 613-620, Portland Press, England (2003).

Gurney, M.E., et al., "Motor Neuron Degeneration in Mice that Express a Human Cu, Zn Superoxide Dismutase Mutation," *Science* 264(5166): 1772-1775, American Assn. for the Advancement of Science, United States (1994).

Haase, G., et al., "Therapeutic Benefit of Ciliary Neurotrophic Factor in Progressive Motor Neuronopathy Depends on the Route of Delivery," *Ann. Neurol.* 45(3): 296-304, Wiley-Liss, United States (1999).

Larsen, K.E., et al., "A Glial Cell Line-Derived Neurotrophic Factor (GDNF):Tetanus Toxin Fragment C Protein conjugate Improves Delivery of GDNF to Spinal Cord Motor Neurons in Mice," *Brain Research* 1120(1): 1-12, Elsevier/North-Holland Biomedical Press, Netherlands (2006).

McFerran, B.W., et al., "Neuronal $Ca^{2+}$ Sensor 1, the Mammalian Homologue of Frequenin, is Expressed in Chromaffin and PC12 cells and Regulates Neurosecretion from Dense-core Granules," *J. Biol. Chem.* 273(35): 22768-22772, American Society for Biochemistry and Molecular Biology, United States (1998).

McHanwell, S., et al., "The Localization of Motoneurons Supplying the Hindlimb Muscles of the Mouse," *Philos. Trans. R. Soc. Lond. B Biol. Sci.* 293: 477-508, Royal Society of London, England (1981).

Navarro, X., et al., "Comparison of Regenerative and Reinnervating Capabilities of Different Functional Types of Nerve Fibers." *Exp. Neurol.* 129: 217-224, Academic Press, United States (1994).

Penas, C., et al., "Cytoskeletal and Activity Related Changes in Spinal Motoneurons After Root Avulsion," *J. Neurotrauma* 26: 763-779, Mary Ann Liebert, United States (2009).

(Continued)

*Primary Examiner* — Robert C Hayes
(74) *Attorney, Agent, or Firm* — Sterne, Kessler, Goldstein & Fox P.L.L.C.

(57) ABSTRACT

The present invention relates to the therapeutic use of the carboxy-terminal domain of the heavy chain of the tetanus toxin for the treatment of amyotrophic lateral sclerosis (ALS).

9 Claims, 13 Drawing Sheets

(56) References Cited

OTHER PUBLICATIONS

Sakowski, S.A., et al., "Insulin-like Growth Factor-I for the Treatment of Amyotrophic Lateral Sclerosis." *Amyotroph. Lateral Scler.* 10(2): 63-73, Informa Healthcare, England (2009).

Schaad, N.C., et al., "Direct Modulation of Calmodulin Targets by the Neuronal Calcium Sensor NCS-1," *Proc. Natl. Acad. Sci. USA* 93(17): 9253-9258, National Academy of Sciences, United States (1996).

Tu, P.H., et al.,"Transgenic Mice Carrying a Human Mutant Superoxide Dismutase Transgene Develop Neuronal Cytoskeletal Pathology Resembling Human Amyotrophic Lateral Sclerosis Lesions," *Proc. Natl. Acad. Sci. USA* 93(7): 3155-3160, National Academy of Sciences, United States (1996).

Udina, E., et al., "FK506 Enhances Regeneration of Axons Across Long Peripheral Nerve Gaps Repaired with Collagen Guides Seeded with Allogeneic Schwann Cells," *Glia* 47: 120-129, Wiley-Liss, United States (2004).

Verdu, E., et al., "Functional Changes of the Peripheral Nervous System with Aging in the Mouse." *Neurobiology of Aging* 17(1): 73-77, Elsevier, United States (1996).

English Translation of International Search Report for International Application No. PCT/ES2008/070186, Oficina Espanola de Patentes y Marcas, Spain, mailed on Feb. 9, 2009.

International Preliminary Report on Patentability for Application No. PCT/ES2008/070186, European Patent Office, Munich, Germany, mailed on Jan. 29, 2010.

Bordet, T., et al. "Protective effects of cardiotrophin-1 adenoviral gene transfer on neuromuscular degeneration in transgenic ALS mice," *Human Molecular Genetics* 17(18): 1925-1933, Oxford University Press, United Kingdom (2001).

Chaib Oukadour, I., et al. "The C-terminal domain of the heavy chain of tetanus toxin rescues cerebellar granule neurons from apoptotic death: involvement of phsophatidilinositol 3-kinase and mitogen-activated protein kinase pathways," *Journal of Neurochemistry* 90(5): 1227-1236, Wiley Interscience, United States (2004).

Chian, R., et al., "Insulin-like growth factor-1:tetanus toxin fragment C fusion protein for improved delivery of IGF-1 to the CNS," (Abstract No. 413.14) 33rd Annual Meeting of the Society for Neroscience, New Orleans, LA, United States; Nov. 8-12, 2003.

Longstreth, W.T., et al., "Hypothesis: A motor neuron toxin produced by a clostridial species residing in gut causes ALS" *Medical Hypotheses* 64(6): 1153-1156, Eden Press, United States (2005).

Moreno-Igoa, M., et al. "Fragment C of 1-17 tetanus toxin, more than a carrier. Novel perspectives in non-viral ALS gene therapy," *Journal of Molecular Medicine* 88(3): 297-308, Springer, Germany (2009).

Supplemental European Search Report and Search Opinion for European Application No. 08836703.2, European Patent Office, Munich, Germany, mailed on Nov. 12, 2010.

* cited by examiner

THERAPEUTIC USE OF THE ENCODING SEQUENCE OF THE CARBOXY-TERMINAL DOMAIN OF THE HEAVY CHAIN OF THE TETANUS TOXIN

RELATED APPLICATIONS

This application is a continuation-in-part of International Appl. No. PCT/ES2008/070186, filed Oct. 3, 2008.

REFERENCE TO SEQUENCE LISTING SUBMITTED ELECTRONICALLY

The content of the electronically filed sequence listing, file name: 29080010001_Sequence_listing.txt; Size: 12,541 bytes; Date of Creation: Jun. 23, 2010, filed herewith, is incorporated herein by reference in its entirety

BACKGROUND OF THE INVENTION

Amyotrophic Lateral Sclerosis (Lou Gehrig's or Charcot's disease) is a progressive, incurable and fatal disease wherein the motor neurons degenerate at the spinal, bulbar and motor cortex level. In the case of Spain, incidence of the disease is 2/100,000 with a prevalence of 1/10,000, indicating that approximately 40,000 Spaniards will develop the disease in the course of their life (source: Spanish Association of Amyotrophic Lateral Sclerosis—ADELA—).

Despite having been recognized as a disease a long time ago, its causes are still unknown. Although there are genetic forms of the disease, there are also known cases where there does not appear to be a hereditary origin. Thus, it is estimated that 10% of cases, known as family forms, are of genetic origin, of which 15-20% correspond to mutations in the Super Oxide Dismutase enzyme (SOD-1). Mutations of this enzyme have also even been observed in sporadic forms of the disease (Brown, 1997). Mutations in the Neuro Filament Heavy-chain gene (NFH), have also been found unfrequently in some patients with amyotrophic lateral sclerosis. Consequently, research into the genetic inheritance of this disease is of great interest.

In recent years, the creation of animal models of the disease has become one of the most relevant tools in experimental treatment studies, serving to clarify some questions about its causes, although these causes are still largely unknown. Neither knockout mice for the SOD-1 enzyme, nor transgenic animals for the different mutations in the human SOD-1 enzyme have managed to reproduce similar clinical symptoms to the disease in humans. The animal that best approaches the progress of the disease in humans is a transgenic mouse, known as SOD1G93A, that presents various copies of mutant Super Oxide Dismutase with a Glycine to Alanine point mutation in amino acid 93, (Tu et al, 1996) which is supplied by The Jackson Laboratory, Despite numerous studies carried out to understand the cause and mechanism of the disease, at this point, there are no classic effective treatments. Currently, three lines of research are under development based on the application of glutamate antagonists, neurotrophic factors, and antioxidants, even though to date none of them has lead to an efficient treatment.

For several years it has been known that neurotrophic factors are capable of rescuing motor neurons from degeneration. The experiences with gene therapy using adenoviral vectors that express various neurotrophic factors (e.g., GDNF, CNTF, NI-4, IGF-1) carried out on animal models have been of great interest, and have offered promising results. However, adenoviral injections present the disadvantage of having to be applied to neonatal animals due to the great immunity response that they elicit. Therefore, although these results have been promising, developing novel but less immunogenic vectors is imperative in order to provide an effective treatment for ALS.

In regard to the clinical tests carried out to date, those initiated in 1996 by Dr. Schuelp did not achieve satisfactory results (http://www.wiley.co.uk/genetherapy). Possible causes of this failure were the nature of the neurotrophic factor used in the tests (Ciliary Neurotrophic Factor; CNTF) and/or its lack of accessibility to the Central Nervous System. In 1999, Dr. Axel Kahn's group proved in model animals that the administration route of CNTF is an important factor for its therapeutic effect (Haase et al., 1999). This lack of specificity has also been proposed as the probable cause for the failure of the subcutaneous administration of BDNF (Bovine-Derived Neurotrophic Factor) to humans.

Moreover, when the neurotrophic factors are administered systemically they present toxicity problems by acting upon other tissues. Despite all of these disadvantages, the therapeutic possibilities of neurotrophic factors continue to be researched due to their promising pre-clinical results. Specifically, the latest clinical trial taking place in the Medical Center of Rochester (Minnesota) is based again on the administration of a neurotrophic factor, IGF-1 (Insulin-like Growth Factor 1)(Sakowshi et al., 2009).

SUMMARY OF THE INVENTION

Tetanus toxin is a potent neurotoxin. Structurally, tetanus toxin (150 kDa) is comprised of two polypeptide chains, a heavy chain (100 kDa) and a light chain (50 kDa). One disulfide bridge connects these two polypeptides. The heavy chain contains the toxin's binding and translocation domains, whereas the light chain is a protease which cleaves synaptobrevin. The toxin first binds to gangliosides on peripheral nerve endings and is internalized through receptor-mediated endocytosis. The toxin then travels to the ventral horn by axoplasmic transport. From there it is released into the interneuronal space and is subsequently taken up by the inhibitory interneurons adjacent to the soma of the motor neurons. An important fragment, the tetanus toxin C-fragment, is generated when the toxin is enzymatically cleaved by papain. This C-fragment (50 kDa) corresponds to the 451 amino acids at the C-terminus of the tetanus toxin heavy chain. The C-fragment is useful because it retains the binding, internalization and trans-synaptic transport capabilities of the whole toxin. However it is nontoxic since it does not disrupt any neuronal processes.

The authors of the present invention have discovered that the non-toxic carboxy-terminal domain of the heavy chain of the tetanus toxin (HcTeTx), which to date had only been used in the treatment of ALS as a vehicle for various neurotrophic factors (Ciriza et al., 2008b) and the enzyme SOD-1 (Francis et al., 2004), through the creation of fusion proteins (Ciriza et al., 2008a, 2008b), is by itself capable of prolonging the survival of animal models of the disease.

Thus, a first aspect of the invention relates to the use of a polynucleotide comprising the encoding sequence of isolated HcTeTx, its allelic variants or functional fragments thereof for the manufacture of a drug to treat or ameliorate a neuronal degenerative disease of spinal, bulbar and motor cortex motor neurons, preferably for the treatment of ALS. In another embodiment of the invention the encoding sequence of HcTeTx comprises the polynucleotide sequence from the codon encoding the amino acid V (Valine) at the amino terminal end of HcTeTx, to the codon encoding the amino acid D (Aspartate) at the carboxy terminal of HcTeTx, preferably from the codon for amino acid V(854) to the codon for amino acid D(1315) of the protein sequence with access number (NCBI.: P04958; tetanus toxin precursor, containing both Hc and Lc). In another embodiment of this aspect of the invention the encoding sequence of HcTeTx is SEQ ID NO: 1 and the encoded sequence of the HcTeTx fragment is SEQ ID NO: 6. Hereinafter, this polynucleotide will be referred to as the “polynucleotide of the invention”.

In another embodiment, the polynucleotide of the invention may comprise mutations (deletions, insertions, inversions, point mutations, etc.) wherein said mutations do not affect its capacity to act as a drug, specifically for the treatment of ALS. Maintenance of the therapeutic effect of the mutated polynucleotide of the invention may be tested by reproducing any of examples 1 and 2. Throughout the description, these mutated polynucleotides will also be considered as allelic variants.

In another embodiment, the polynucleotide of the invention may comprise additionally promoter, terminator, and/or silencer sequences, sequences that facilitate its integration in chromosomes or any type of organizational structure of genetic material, etc.

Another aspect of the invention refers to the use of a vector that comprises the polynucleotide of the invention for the manufacture of a drug to treat or ameliorate a neuronal degenerative disease of spinal, bulbar and motor cortex motor neurons, preferably for the treatment of ALS, wherein said vector is selected from the group consisting of plasmids, phages, cosmides, phagemids, yeast artificial chromosomes (YAC), bacterial artificial chromosomes (BAC), human artificial chromosomes (HAC), viral vectors, such as adenoviruses, retroviruses and any other type of DNA or RNA molecule capable of self-replication. Hereinafter, this vector will be referred to as the “vector of the invention”.

Another aspect of the invention relates to the use of a transgenic cell for the creation of a drug, preferably for the treatment of ALS, wherein said cell comprises the polynucleotide of the invention or the vector of the invention.

Another aspect of the invention relates to the use of an isolated polypeptide comprising the sequence of HcTeTx, its allelic variants or functional fragments thereof for the manufacture of a drug to treat or ameliorate a neuronal degenerative disease of spinal, bulbar and motor cortex motor neurons, preferably for the treatment of ALS. In an embodiment of the invention, the sequence of the HcTeTx polypeptide comprises from amino acid V(854) to D(1315) of the sequence with access number (NCBI: P04958; tetatus toxin precursor, containing both tetanus toxin Lc and Hc). In another embodiment of this aspect of the invention, the sequence of HcTeTx is SEQ ID NO: 2 and the sequence of the fragment of HcTeTx is SEQ ID NO: 5. Hereinafter, this polynucleotide will be referred to as the “polypeptide of the invention”.

In another embodiment, the polypeptide of the invention is mutated (deletion, insertion, inversion, point replacements of amino acids, etc.), although said mutations do not affect its capacity to act as a drug in the treatment of ALS. Maintenance of the therapeutic effect of the mutated polypeptide of the invention may be tested by reproducing Examples 1-2.

For the administration of the drug or pharmaceutical composition the polynucleotide, vectors, transgenic cells or polypeptide of the invention will be formulated in a suitable pharmaceutical form for administration via the selected route of administration. To this effect, said pharmaceutical composition will include the pharmaceutically acceptable vehicles and excipients necessary for the manufacture of the pharmaceutical form of the selected administration. Information regarding excipients or vehicles that may be used in the manufacture of said pharmaceutical composition, and also regarding pharmaceutical forms of administering active principles, in general, can be found in the book “Treaty of Galenic Pharmacy”, by C. Fauli i Trillo, $1^{St}$ Edition, 1993, Luzan 5, S.A. de Ediciones.

Said pharmaceutical composition consists of, at least, any of the elements of the group that comprises: the polynucleotide, vectors, transgenic cells or polypeptide of the invention in therapeutically effective amounts. In the sense used in this description “therapeutically effective amount” refers to the amount of the selected element calculated to produce the required effect and, in general, will be determined, among other reasons, by the inherent properties of the polypeptide element itself and the therapeutic effect to be achieved, the characteristics of the individual under treatment, the severity of the disease suffered by the individual in question, etc. Hereinafter, this pharmaceutical composition will be referred to as “pharmaceutical composition or drug of the invention”.

The pharmaceutical composition of the invention may be administered by any appropriate route of administration, for example, oral, intravenous, nasal (mucous), etc., typically, intravenous, beneficially, by means of intramuscular or subcutaneous administration. At the same time, said pharmaceutical composition may appear in any appropriate form of presentation for its administration, for example, in solid presentation form (tablets, capsules, granules, etc.), liquid (solutions, suspensions, emulsions, etc.), etc., for its administration via the selected administration route. In one embodiment, said pharmaceutical composition is formulated in the pharmaceutical form of an appropriate unitary dose.

In another embodiment, the pharmaceutical composition may be in a pharmaceutical form for oral administration, either in solid form, preferably liquid, more preferably ready for intramuscular administration. Illustrative examples of pharmaceutical forms for oral administration include tablets, capsules, granulate, solutions, suspensions, etc., and may contain the conventional excipients, such as binding agents, diluting agents, disintegrating agents, lubricating agents, humidifiers, etc., and may be prepared by conventional methods.

In another embodiment, the pharmaceutical compositions may also be adapted for intravenous administration, for example, in the form of solutions, suspensions or sterile lyophilized products, in the appropriate form of dose; in this case, said pharmaceutical compositions will include the appropriate excipients, such as buffers, surfactants, etc. In any case, the excipients will be chosen according to the selected pharmaceutical form of administration.

A review of the different pharmaceutical forms of administration and of their preparation can be found in the book “Treaty of Galenic Pharmacy”, by C. Fauli i Trillo, $1^{St}$ Edicion, 1993, Luzan 5, S.A. de Ediciones, mentioned above. Also, the pharmaceutical composition may comprise other polypeptides, polynucleotides, vectors or cells that make the composition more effective.

In an embodiment, the polynucleotides and vectors of the present invention are administered as naked DNAs.

In another aspect of the invention the polypeptides, polynucleotides, cells, vectors, or compositions of the invention or combinations thereof may be used as neuroprotectants to treat a neuronal disease, disorder, or condition of peripheral motor neurons.

BRIEF DESCRIPTION OF THE DRAWINGS

FIG. 12 shows the amplitude of M waves in hindlimb muscles of SOD1G93A mice at 12 and 16 weeks of age. Figure panels show representative recordings of M waves recorded from tibialis anterior muscles.

FIG. 13 shows motor neuron survival in SOD1G93A mice.

FIG. 14 presents an analysis of glial reactivity in SOD1G93A mice.

DETAILED DESCRIPTION OF THE INVENTION

Figure 1:
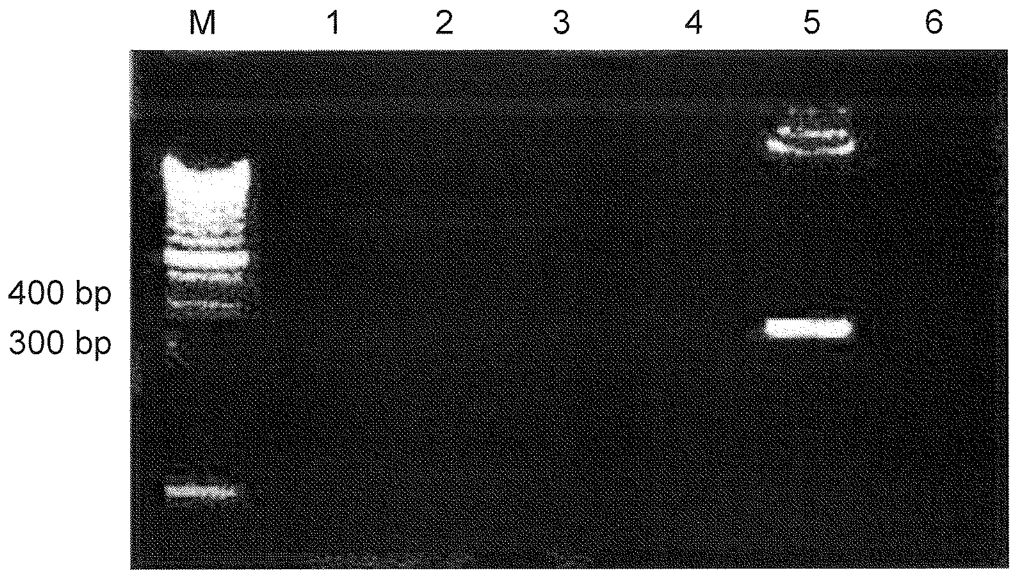
FIG. 1 shows PCR amplification for the detection of the expression of HcTeTx. Ten days after intramuscular injection of the plasmid pCMV-HcTeTx (n=2, lanes 1 and 2) and of the empty plasmid pCMV (n=2, lanes 3 and 4) the RNA was extracted from the muscle and retrotranscribed. The obtained cDNA was amplified by PCR for the HcTeTx gene. Lane 5 shows the positive control (pCMV-HcTeTx plasmid) and the reaction blank was run in lane 6. In lane M we find the size marker of 100 bp.

Next is an illustration of the invention through the tests carried out by the inventors, which make manifest the effectiveness of HcTeTx, in addition to its encoding sequence, for use as a drug, preferably for the treatment of ALS.

DEFINITIONS

The term "polynucleotide", as used in this description refers to a polymeric form of nucleotides of any length, either deoxyribonucleotides or ribonucleotides. This term refers exclusively to the primary structure of the molecule. Hence, this term includes bi- and mono-catenary DNA, as well as bi- and mono-catenary RNA.

The term "isolated" throughout the description when used in association with HcTeTx or its encoding sequence, refers not only to the fact that these are isolated from the human body, but also that they do not form part of fusion proteins or enzymes that may carry out a therapeutic function. In some preferred embodiments, HcTeTx is not isolated, but forms part of fusion proteins or enzymes that carry a therapeutic function, provided that the HcTxTe moiety does not function as a vehicle, carrier, or transporter for targeted delivery to neuronal cells. In those constructs, the non-HcTeTx moiety of the fusion construct may have a therapeutic or non-therapeutic function.

The expression "functional fragment of HcTeTx, allelic variants thereof or their encoding sequences" refers throughout the description to a peptide or polynucleotide comprising a portion of HcTeTx, its allelic variants or encoding sequences, which maintain their capacity to act as a drug, more specifically for the treatment of ALS, wherein the maintenance of their therapeutic capacity can be checked by reproducing examples 1-3.

The term "allelic variant" refers throughout this description to a polypeptide that is substantially homologous and functionally equivalent to the C-terminal domain of the heavy chain of the tetanus toxin. As used herein, a peptide is "substantially homologous" to said domain when its sequence of amino acids has a degree of similarity in respect of the sequence of amino acids of said domain, of at least 60%, 70%, 85% and, more preferably of at least 95%. Preferably, the amino acid sequence of the cited domain is SEQ ID NO: 2. This term also refers in the description to a polynucleotide capable of encoding a polypeptide substantially homologous and functionally equivalent to HcTeTx. In this way, the polynucleotide may be homologous by at least 40%, 50%, 60%, 70%, 85% or 95% to the encoding polynucleotide of HcTeTx, whose nucleotide sequence is preferably SEQ ID NO: 1.

The expression "functionally equivalent", as used throughout the description, means that the polypeptide or the polypeptide maintains its capacity to act as a drug, more specifically for the treatment of ALS, wherein maintenance of its therapeutic capacity can be checked by reproducing example 1 or 2.

For experts in the art, other objects, benefits and characteristics of the invention will be inferred partly from the description and partly from the practice of the invention. The following examples are provided by way of illustration and are not intended to limit this invention.

Example 1

The Administration of HcTeTx by Intramuscular Injection of Naked DNA Delays the Start of Symptoms and Prolongs the Survival of SOD1G93A Mice The generation of transgenic animals that over-express the human gene for Superoxide Dismutase-1 (SOD-1) with different mutations has provided animal models for the study of ALS. These animals present the same clinical and pathological characteristics as ALS patients. One of the models most studied and characterized models is the SOD1G93A transgenic mouse, which presents a mutation by replacement of the amino acid glycine for alanine in position 93 of the gene encoding SOD-1.

Various therapeutic compounds have been tested successfully on this model. However, in clinical tests on humans they have not resulted in effective therapy, whether due to an inadequate route of administration and/or due to the scarce bioavailability of the therapeutic molecules for reaching the target cells. Some gene therapy strategies include the use of an adeno-associated virus (AAV), which is transported retrogradely to motor neurons following intramuscular injection. However, there is a possibility that the use of viral vectors may cause additional damage to treated patients. The use of naked DNA presents itself as a safer and more appropriate alternative strategy for providing patients with a specific therapeutic gene.

Materials and Methods 1.1 Naked DNA Encoding HcTeTx

The gene encoding HcTeTx (C-terminal domain of the heavy chain of the Tetanus toxin—SEQ ID NO: 2 of 462 amino acids—) was cloned in the eukaryote expression plasmid pcDNA3.1 {Invitrogen), under the control of the promoter of the cytomegalovirus (CMV). The vectors ware produced in chemically competent *Escherichia coli* bacteria (DH5$\alpha$) and were purified using the GenElute maxiprep kit of Sigma-Aldrich.

1.2 Transgenic Mice

SOD1-G93A transgenic mice, which overexpress human SOD1 with the mutation G93A (B6SJL-TgN[SOD1-G93A]1Gur), were obtained from The Jackson Laboratory (Bar Harbor, Me.). Hemizygote mutants were used in all experiments (a mutant male mated with a non-transgenic female). The transgenic mice were identified by PCR amplification of the DNA extracted from the tail, as described in Gurney et al. (1994). The animals were kept in the Mixed Research Unit of Zaragoza University. They were given food and water ad libitum. All experiments and care of the animals were conducted in compliance with the rules of Zaragoza University and of the international guide for the care and use of laboratory animals.

1.3 Intramuscular Injection of Naked DNA and Muscle Extraction

At 8 weeks of age the transgenic SOD1G93A mice were given intramuscular injections of 300 μg of pCMV-HcTeTx in the quadriceps muscles (two injections of 50 μg per muscle) and in the triceps muscles (a single injection of 50 μg per muscle). The control group of mice was injected with the same amounts of empty plasmid. Ten days after the intramuscular injections of the plasmids, the inoculated muscles were extracted, pre-frozen in liquid nitrogen and subsequently stored at −70° C.

1.4 Extraction of RNA, Synthesis of cDNA and Amplification by PCR

The tissues were frozen in liquid nitrogen and then pulverized in a cold mortar and pestle. The muscles total RNA was extracted following the TRIzol Reagent protocol (Invitrogen). For the synthesis of cDNA the kit SuperScript™ First-Strand Synthesis System (Invitrogen) was used, starting out with 1 μg of RNA in a final volume of 20 μL. The PCR reactions were carried out in a final volume of 20 μL, with 150 nM of each primer, 150 μM of dNTPs, 2 mM of $MgCl_2$ 1× buffer, 0.2U Taq pol and 2 μL per reaction of cDNA diluted 10 times for the amplification of a fragment of the gene HcTeTx. All the PCR reactions were carried out in GeneAmp® Thermal Cycler 2720 (Applied Biosystems, Foster City, Calif., USA). The thermal cycle parameters were as follows: incubation at 94° C. during 3 mins and 35 cycles of 94° C. during 30 s, 61° C. during 30 s and 72° C. during 30 s. The presence of the amplification of the HcTeTx gene was observed in an agarose gel at 2% stained with ethidium bromide. The sequences of the used direct and reverse primers were SEQ ID NO: 3 and SEQ ID NO: 4, respectively. The size of amplification corresponds to 355 bp.

1.5 Rotarod, Grid Test and Survival.

The grid test was used to determine the muscular strength and the start of ALS symptoms. The animals carried out this test once a week from the age of 8 weeks. Each mouse was placed on a grid that serves as a lid for conventional cages. The grid was then turned 180° upside down and held at a distance of approximately 60 cm from a soft surface to avoid injury. The latency to fall of each mouse was timed. Each mouse had up to three attempts to hold onto the inverted grid for a maximum of 180 s and the longest period of time was recorded.

The Rotarod test was used to evaluate motor coordination, strength and balance. The animals were placed on the rotating rod of the device (ROTAROD/RS, LE8200, LSI-LETICA Scientific Instruments). The time during which an animal could maintain itself on said bar at a constant speed of 14 rpm was recorded. Each mouse had three chances and the longest period of time without the animals falling from the bar was recorded, taking 180 s arbitrarily as the time limit. The end point in the life of the mice was considered to be when the animal was placed in supine position and was incapable of turning itself around.

Results 2.1 Detection of the Expression of the Plasmid in the Muscle

Initially the capacity was confirmed of the constructed vector pCMV-HcTeTx to express the encoding gene in the muscular cell of the transgenic SOD1G93A mice. Because there is no endogenous expression of the HcTeTx gene in these mice, PCR amplification of a fragment of this gene was applied to the injected muscles in order to detect the expression of the mRNA of said molecule. As shown in FIG. 1, no expression of the HcTeTx gene is observed in the control group injected with empty plasmid. However, the PCR reveals the presence of the amplification of the HcTeTx gene in the muscle inoculated with the vector encoding same, indicating that the vector successfully reaches the muscular cells and that the process of transcription of said gene is carried out.

Figure 2:
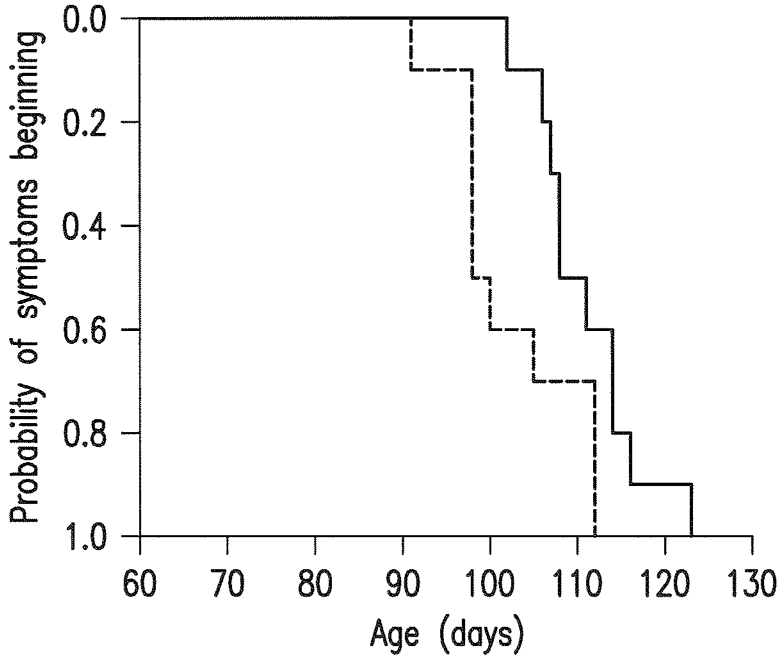
FIG. 2 shows the effects of the treatment with naked DNA encoding HcTeTx on the start of symptoms in model mice for the ALS disease SOD1G93A. The manifestation of symptoms was significantly delayed in the group treated with HcTeTx (n=10) in respect of the control group (n=10). The accumulated probabilities were calculated using the Kaplan-Meier survival analysis (SPSS 13.0).
Figure 3:
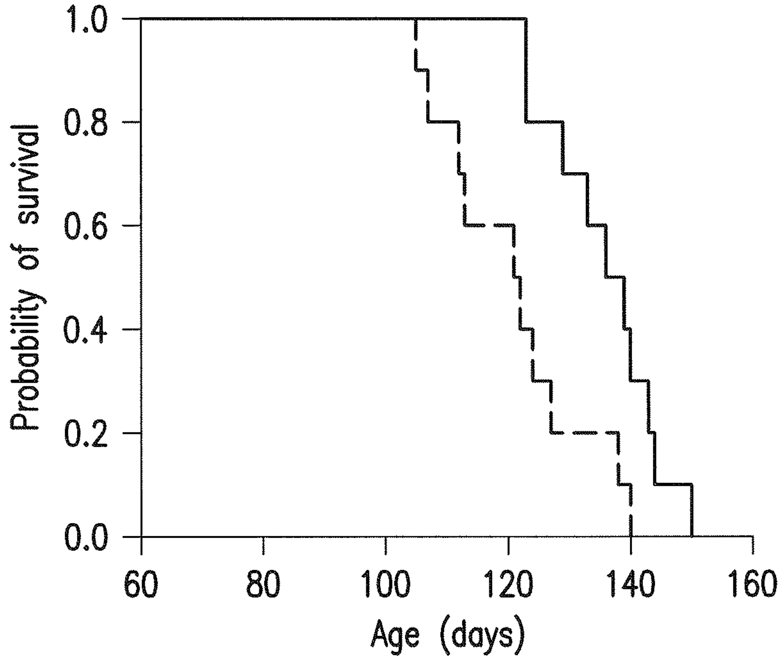
FIG. 3 shows the effects of the treatment with naked DNA encoding HcTeTx on the survival of model mice for the ALS disease SQD1G93A. Survival notably increased in the group treated with HcTeTx (n=10) in respect of the control group (n=10). The accumulated probabilities were calculated using the Kaplan-Meier survival analysis (SPSS 13.0).
Figure 4:
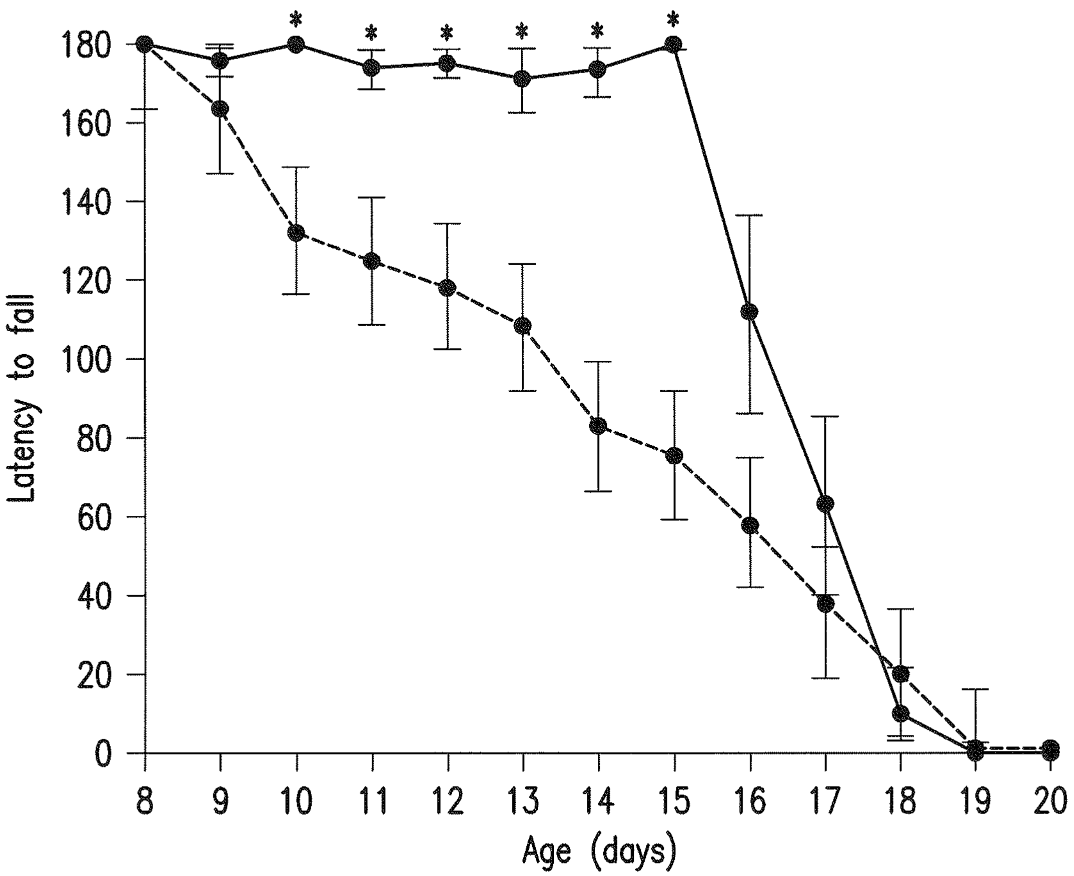
FIG. 4 shows the effects of the treatment with naked DNA encoding HcTeTx. Motor activity was determined using the Rotarod at a constant speed of 14 rpm, with a maximum development time of 180 s. Improved motor activity is observed in the group treated with HcTeTx (n=10) in respect of the control (n=10).

2.2 HcTeTx Delays the Manifestation of Symptoms, Improves the Motor Capacity and Extends the Survival of Transgenic SOD1G93A Mice Intramuscular treatment with naked DNA encoding HcTeTx produces a delay in the start of symptoms, improves motor activity and postpones the end point of the disease in the model mouse for ALS, which contains the G93A mutation in the human SOD1 gene. The manifestation of symptoms was recorded as the first day on which the mice were unable to keep hold of the inverted grid for 3 minutes. The start of symptoms was reduced very significantly by approximately 8 days in the group of animals injected with HcTeTx, in relation to the control group (FIG. 2, and TABLE 1). As we can see from FIG. 3 and TABLE 1, maximum survival was detected in the group of mice treated with HcTeTx, which reached an average of 136 days; 16 days more than the control group. Between weeks 12 and 13 a notable decrease was observed in the development of the Rotarod activity of the control group, whereas in the group of treated animals these deficiencies were not observed until week 16 (FIG. 4).

TABLE 1

Table showing data on the manifestation of symptoms and survival of both the control group and the group treated with HcTeTx, in addition to the P value (Log Rank, Mantel-Cox).

| | Control (n = 10) | HcTeTx (n = 10) | P Value |
|---|---|---|---|
| Start of symptoms (days) | 102.4 ± 2.4 | 110.9 ± 2.0 | 0.0295 |
| Mortality (days) | 120.5 ± 3.9 | 136.0 ± 3 | 0.0093 |
| Difference in start – mortality (days) | 18.1 | 25.1 | |

Figure 5:
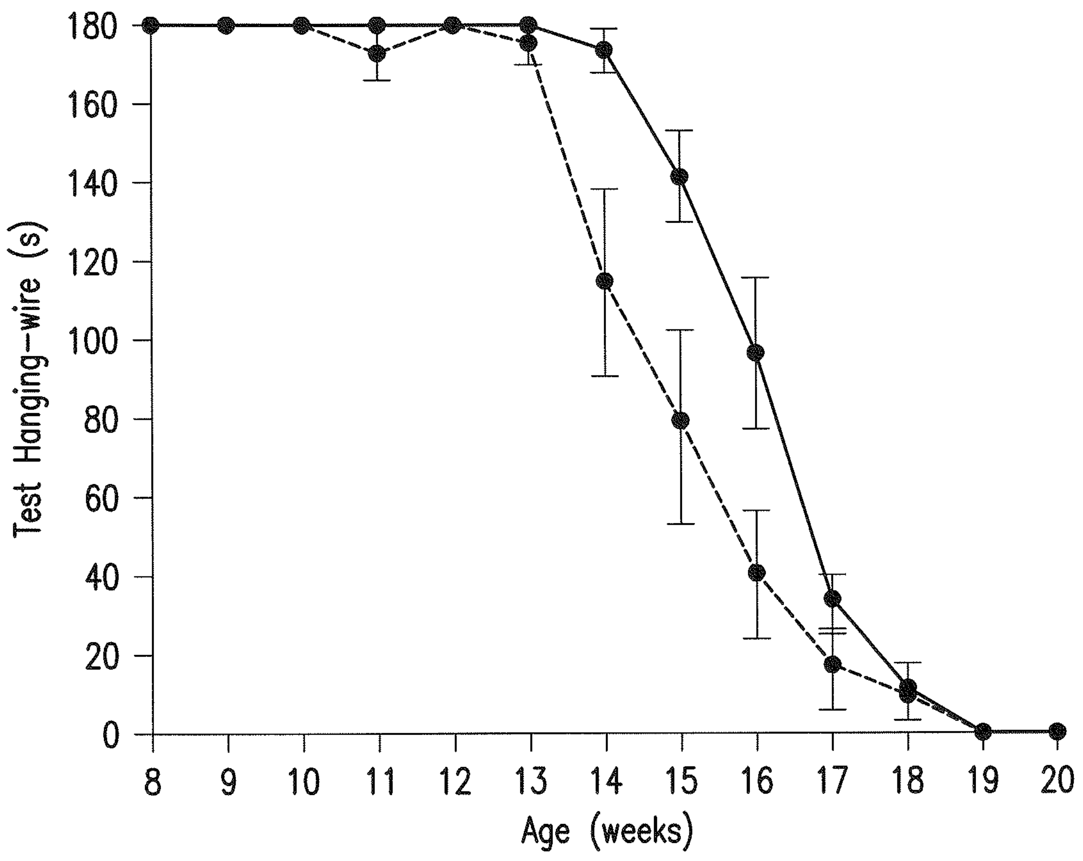
FIG. 5 presents the effect of the intramuscular injection of naked DNA encoding HcTeTx in SOD1G93A mice. The strength and motor function of the mice were tested with the hanging-wire test using 10 mice from each group (n=10).
Figure 6:
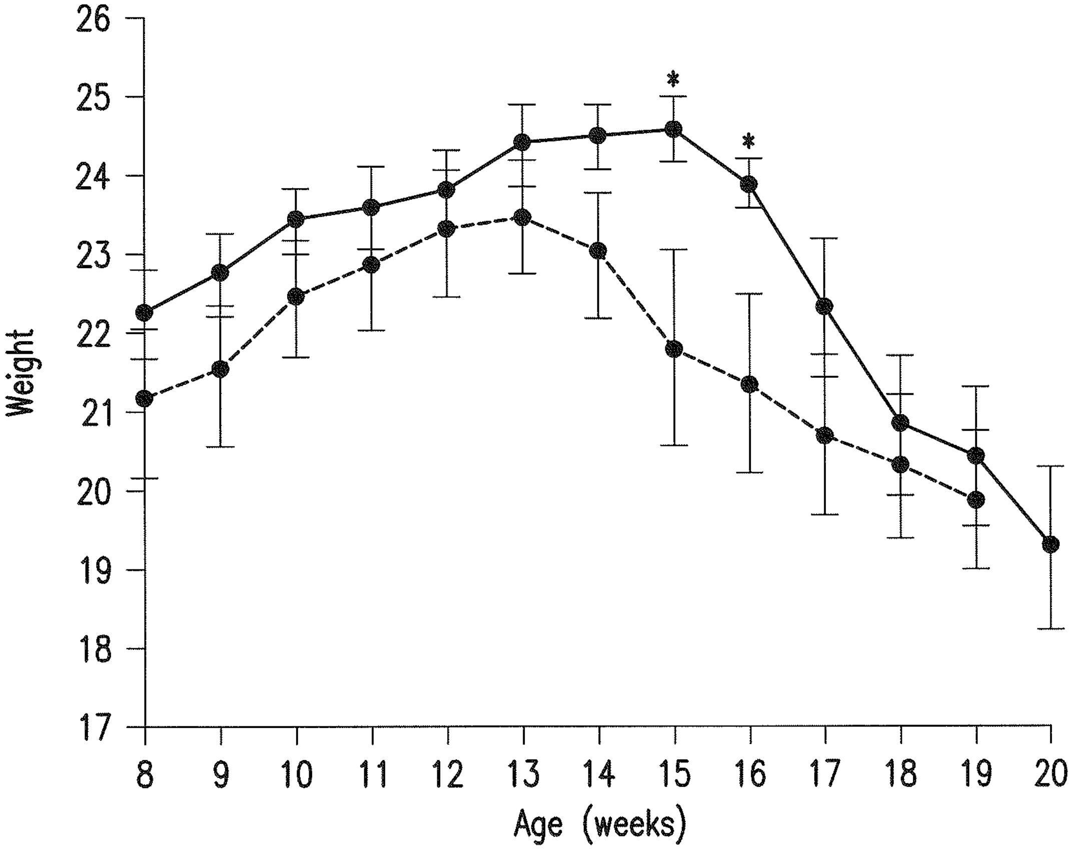
FIG. 6 presents the effect of the intramuscular injection of naked DNA encoding HcTeTx in SOD1G93A mice. Measurement of the weight of the transgenic mice treated with HcTeTx using 10 mice from each group (n=10).

The treatment was also evaluated in mice starting at 8 weeks of age using the “hanging-wire” test (FIG. 5). At 14 weeks of age, the SOD1G93A mice showed the first signs of weakness, whereas the group of mice treated with HcTeTx proved to be more resistant between weeks 14-16. Also, the mice of the control group started to lose weight as of 14 weeks of age associated to the disease. However, the treatment with HcTeTx significantly counteracted the weight loss, showing a maximum weight at 15 weeks (FIG. 6).

Example 2

Inhibition of Apoptosis in the Spinal Cord of SOD1G93A Mice Treated by Intramuscular Injection of Naked DNA Encoding HcTeTx Materials and Methods 1.1 Naked DNA Encoding HcTeTx The gene encoding HcTeTx (C-terminal domain of the heavy chain of the Tetanus toxin, SEQ ID NO: 1) was cloned in the eukaryote expression plasmid pcDNA3.1 (Invitrogen), under the control of the promoter of the cytomegalovirus (CMV). The vectors were produced in chemically competent *Escherichia coli* bacteria (DH5α) and were purified using the Genelute maxiprep kit of Sigma-Aldrich.

1.2 Transgenic Mice

The transgenic mice that overexpress human SOD1 with the mutation G93A (B6SJL-TgN[SOD1-G93A]1Gur) were obtained from The Jackson Laboratory (Bar Harbor, Me.). Hemizygote mutants were used in all experiments (a mutant male mated with a non-transgenic female). The transgenic mice were identified by PCR amplification of the DNA extracted from the tail, as described in Gurney et al. (1994). The animals were kept in the Mixed Research Unit of Zaragoza University. They were given food and water ad libitum. All experiments and care of the animals were conducted in compliance with the rules of Zaragoza University and of the international guide for the care and use of laboratory animals. A total of 12 animals were used: wild-type (n=5), SOD1G93A mice injected with pcDNA3.1 (control, n=5) and SOD1G93A mice treated with HcTeTx (n=5).

1.3 Intramuscular Injection of Naked DNA and Spinal Cord Extraction

At 8 weeks of age the transgenic SOD1G93A mice were given intramuscular injections of 300 μg of pCMV-HcTeTx in the quadriceps muscles (two injections of 50 μg per muscle) and in the triceps muscles (one single injection of 50 μg per muscle). The control group of mice was injected with the same amounts of empty plasmid, The spinal cords were extracted 110 days after the intramuscular injections of the plasmids. pre-frozen in liquid nitrogen and subsequently stored at −70° C. The tissues were frozen in liquid nitrogen and then pulverized in a cold mortar and pestle. Half of the sample was used for RNA extraction and the other half was used for protein extraction.

1.4 RNA Extraction from the Spinal Cord and Synthesis of cDNA

Spinal cord total RNA was extracted following the RNeasy® Lipid Tissue Mini Kit protocol (Qiagen). For the synthesis of cDNA the SuperScript™ First-Strand Synthesis System kit (Invitrogen) was used, starting out with 20 μg of RNA in a final volume of 20 μL.

1.5 Real Time PCR

The real time PCR reactions were carried out in a final volume of 10 μL. with IX TaqMan® Universal PCR Master Mix. No AmpErase® UNG (Applied Biosystems). 1× the mixture of unmarked primers and TaqMan® MGB probes (Applied Biosystems) for each gene under study and 1 μL per reaction of cDNA diluted 10 times. For normalization, 3 endogenous genes were used (18s rRNA, GAPDH and β-actin). The references of the mixture of primers and probes used to amplify each one of the genes under study were as follows: caspase-3 (Mm01195085_ml), caspase-1 (Mm00438023_ml), NCS-1 (Mm00490552_ml), Rrad (Mm00451053_ml), 18s rRNA (Hs99999901), GAPDH (4352932E) and β-actin (4352933E). All the PCR reactions were carried out in an ABI Prism 7000 Sequence Detection System thermocycler (Applied Biosystems). The thermal cycle parameters were as follows: incubation at 95° C. during 10 mM and 40 cycles of 95° C. during 15 s and 60° C. during 1 min. The relative expression of caspase-3, caspase-1, NCS-1, and Rrad was normalized by applying the geometric mean value of the three endogenous genes.

1.6 Spinal Cord Protein Extraction and Western Blot Analysis

The spinal cord samples of wild type mice and SOD1G93A mice treated with HcTeTx were homogenised in liquid nitrogen with the extraction buffer consisting of 150 mM NaCl, 50 mM Tris-HCl pH7.5, 1% desoxycholate, 0.1% SDS, 1% Triton X-100, 1 mM NaOVa, 1 mM PMSF, 10 μg/mL leupeptin and aprotinin and 1 μg/mL pepstatin. It was centrifuged at 4° C., during 10 minutes at 3,000×g. After quantifying the concentration of protein in the supernatant of each sample using the BCA method (9643 Sigma), 25 μg of protein were loaded in a gel at 10% of acrylamide. PVDF membranes were used for the transfer, which were blocked with TTBS solution at 5% skimmed milk (20 mM Tris base, 0.15M NaCl, pH=7.5, 0.1% Tween) during one hour. Later they were incubated with the primary antibody all night at 4° C. (anti-GAPDH (sc-25778, Sta. Cruz)).

Following incubation with the primary antibody, the membranes were washed with TTBS and incubated with the secondary antibody for 1 hour at room temperature. Finally, there was revelation by chemiluminescence (Western Blotting Luminol Reagent, sc-2048 Sta. Cruz). The films were scanned and analyzed using the AlphaEase FC (Bonsai Technologies). The statistical analysis was carried out using the ANOVA test and the Student-Neuman-Keuls test.

Results

Figure 7:
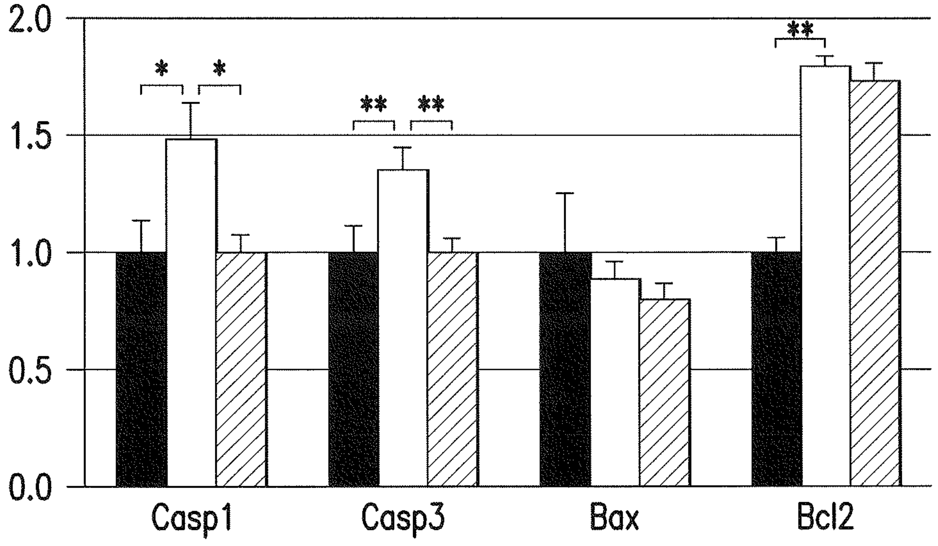
FIG. 7 shows the analysis of the expression of genes involved in the signaling route of apoptosis in the spinal cord of symptomatic SOD1G93A mice of 110 days of age. Representation of the average values of messenger RNA of genes Casp1, Casp3, Bax and Bc12 in the control (white) and in the mice treated with HcTeTx (grey). The previous groups of mice were compared with wild-type mice (black) (n=5 mice per group).

This study presents the results of the application of HcTeTx on model SOD1G93A mice for the ALS disease, where there is a degeneration of the motor neurons. The transcriptional study at the level of the spinal cord of these mice, of symptomatic age, appears in FIG. 7, comparing the transcriptional regulation of the genes caspase-1 ($P<0.05$), caspase-3 ($P<0.05$), and Bc12 ($P<0.01$), but no significant difference was found in the expression profile of the gene Bax ($P>0.05$) in control SOD1G93A mice when compared to the wild type (FIG. 7).

In the group of mice that received treatment with HcTeTx, the levels of expression of caspase-1 and caspase-3 were maintained in the wild type and significant differences were only found when they were compared to the group of untreated mice ($P<0.05$ and $P<0.01$, respectively). However, the expression of the genes Bax and Bc12 was not affected by the treatment of HcTeTx ($P>0.05$) in the spinal cords of these transgenic mice (FIG. 7)

Figure 8:
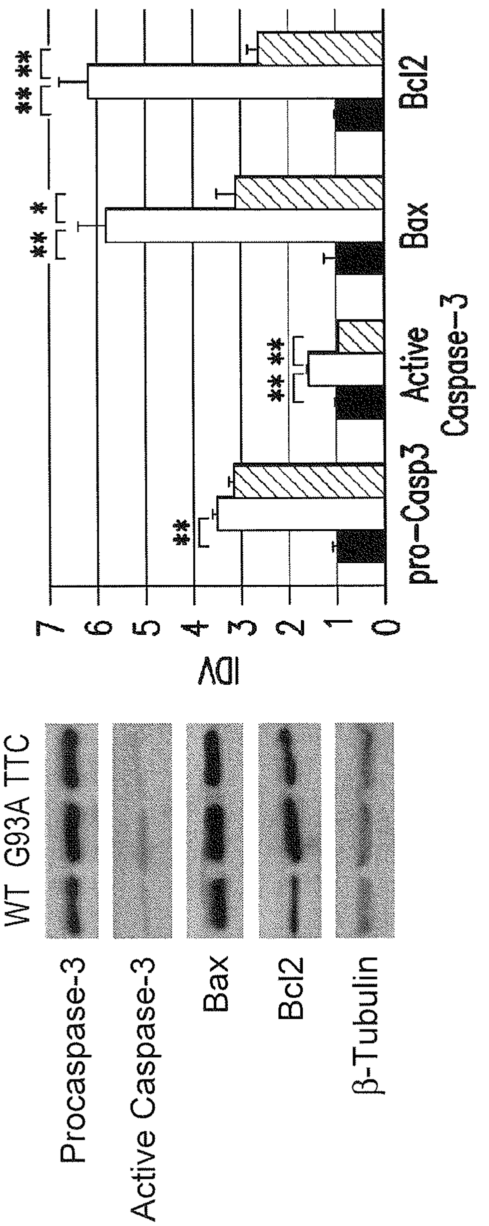
FIG. 8 presents analysis of the proteins involved in the signalling route of apoptosis in the spinal cord of symptomatic SOD1G93A mice of 110 days of age. Western-blot analysis of the proteins pro-Casp3, active Casp3, Bax and Bc12 on spinal cord lysates of mice treated with HcTeTx (grey lines) and control mice (black lines) in relation to wild-type mice (black) (n=5 mice per group).

In order to evaluate the effects of HcTeTx on the mechanisms that reverse apoptosis which can induce cell death in the spinal cord of the SOD1G93A mice, a protein study was also carried out. The data revealed that the activation of the caspase-3 gene ($P<0.05$) decreased perceptibly in the mice treated with HcTeTx in relation to the control group, reaching similar levels to those of wild-type mice, whereas the levels of the pro-caspase-3 protein were not affected in the transgenic animals. In contrast to the results obtained from the expression analysis, in the Western blot it was observed that the proteins Bax and Bc12 were in lesser amounts in the mice treated with HcTeTx (FIG. 8).

Figure 9:
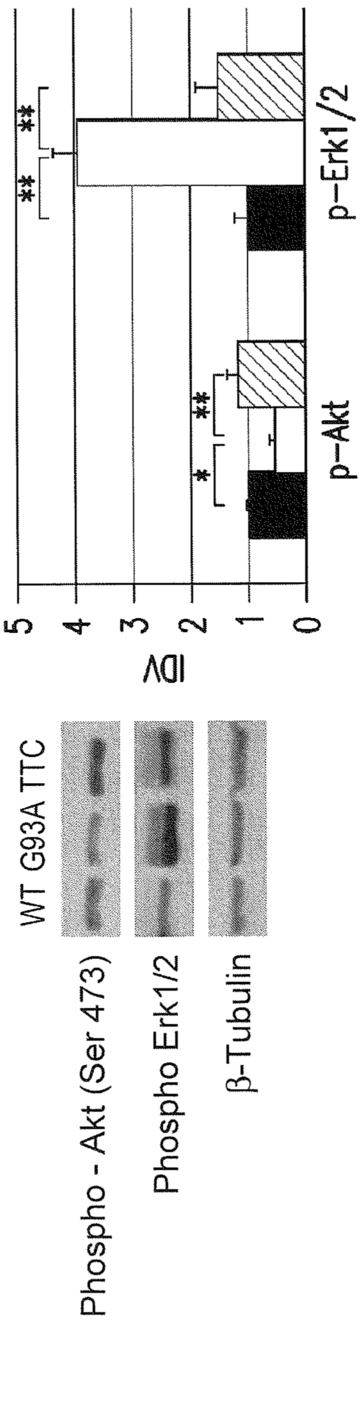
FIG. 9. shows a Western-blot analysis of the phosphorylation of proteins Akt and Erk1/2. Samples of 5 mice per group were analyzed. IDV (Intensity Density Value). The amounts analyzed using the Western-blot appear as the ration of beta-tubulin in respect of the values of the wild-type mice. (*P<0.05, **P<0.01; the error bars show SEM). The bars represent the same groups as described in the previous caption.

An action mechanism of HcTeTx is the phosphorylation of Akt (Gil et al., 2003), a kinase protein that is activated by various growth factors involved in the blocking of routes mediated by phosphatidylinositol 3-kinase. The densitometric quantification indicated that the animals treated with HcTeTx had more than two times the levels of Akt phosphorylated in Ser473 when they were compared to the controls of the empty vector ($P<0.05$), as determined by the Western blot analysis through the use of phospho-specific antibodies (FIG. 9).

The equimolar charge of proteins was confirmed by detection with anti-tubulin antibodies. The phosphorylation of ERK1/2 by HcTeTx in cultivated cortical neurons has been previously divulged (Gil et al., 2003). To confirm the implication of HcTeTx in the MAP kinase route, Western blot analyses were carried out on the spinal cord extracts of the treated and untreated SOD1G93A mice of 110 days of age. The results showed a growing activation of ERK1/2 in control mice when compared to the group treated with HcTeTx (FIG. 9), but the level of expression was similar to that of the wild-type mice.

Example 3

Increase in the Survival of Model SOD1G93A Mice Against Amyotrophic Lateral Sclerosis Following Administration Through Intraperitoneal Injection of a Polypeptide Consisting of the C-Terminal Domain of the Heavy Chain of the Tetanus Toxin (HcTeTx)

Materials and Methods 1.1 Extraction of the Polypeptide Consisting of the C-Terminal Domain of the Heavy Chain of the Tetanus Toxin (HcTeTx1)

The polypeptide used (known as HcTeTx) corresponds to the C-terminal domain of the heavy chain of the Tetanus toxin and comprises the sequence of 451 amino acids (SEQ ID NO: 1) of SEQ ID NO. 2, and has been obtained following the protocol described by Gil et al. (Gil et al., 2003).

1.2 Transgenic Mice

The transgenic mice that overexpress human SOD1 with the mutation G93A (B6SJL-TgN[SOD1-G93A]1 Gur) were obtained from The Jackson Laboratory (Bar Harbor, Me.). Hemizygote mutants were used in all experiments (a mutant male mated with a non-transgenic female). The transgenic mice were identified by PCR amplification of the DNA extracted from the tail, as described in Gurney et al. (1994). The animals were kept in the Mixed Research Unit of Zaragoza University. They were given food and water ad libitum. All experiments and care of the animals were conducted in compliance with the rules of Zaragoza University and of the international guide for the care and use of laboratory animals.

1.3 Intraperitoneal Injection of the Polypeptide in the Animals

At the age of 12 weeks intraperitoneal injections were given to the transgenic SOD1G93A mice with 250 μL at a concentration of 0.5 μM of the polypeptide that consists of the C-terminal domain of the Tetanus toxin (HcTeTx). The injection was repeated weekly throughout life.

1.4 Measurement of the Survival of the Animals.

The end point in the life of the mice was considered to be when the animal placed in a supine position was unable to turn itself around.

Results 2.1.—HcTeTx Prolongs the Survival of Transgenic SOD1G93A Mice

Figure 10:
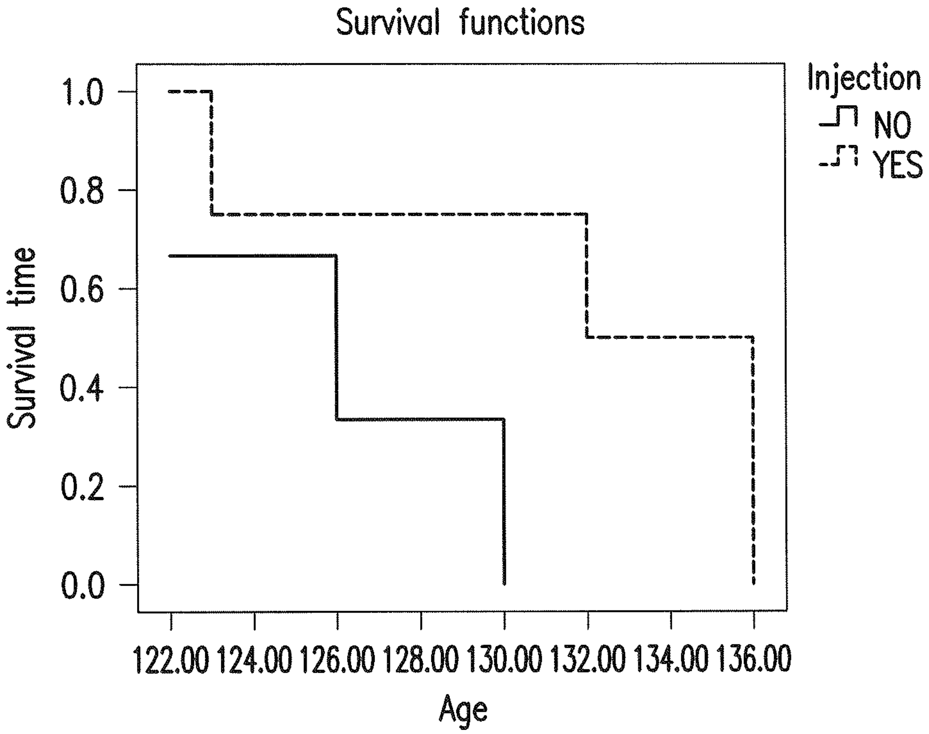
FIG. 10 shows the effects of the-intraperitoneal treatment with the polypeptide containing the C-terminal domain of the heavy chain of the Tetanus toxin (HcTeTx) on the survival of model mice for the ALS disease SOD1G93A. Survival notably increased in the group treated with HcTeTx (n=3, dotted line) in relation to the control group (n=3, continuous line). The accumulated probabilities were calculated using the Kaplan-Meier survival analysis (SPSS 13.0).

As can be seen from FIG. 10 and TABLE 2, maximum survival was detected in the mice from the group treated with HcTeTx, which reached an average of 135 days; 9 more than the control group.

TABLE 2

Showing the survival data of the control group and of the group treated with HcTeTx, in addition to the P value.

| | Control (n = 3) | HcTeTx (n = 3) | P value |
|---|---|---|---|
| Mortality | 126 ± 4 | 135 ± 2 | 0.021 |

Example 4

Administration of HcTeTx Causes Changes in the Expression of Genes Related to the Calcium in the Spinal Cord of SOD1G93A Mice There is evidence of abnormal intracellular homeostasis of calcium related to amyotrophic lateral sclerosis (ALS). It has been proven that neuron protein NCS1 regulates neurosecretion in a calcium-dependent manner (McFerran et al., 1998) and it has also been related to the modulation of the calcium/calmodulin dependent enzymes involved in the neuronal signal transduction (Schaad et al., 1996). The expression was tested of NCS1 of tissues from the spinal cord of SOD1G93A mice 50 days after treatment with HcTeTx.

Figure 11:
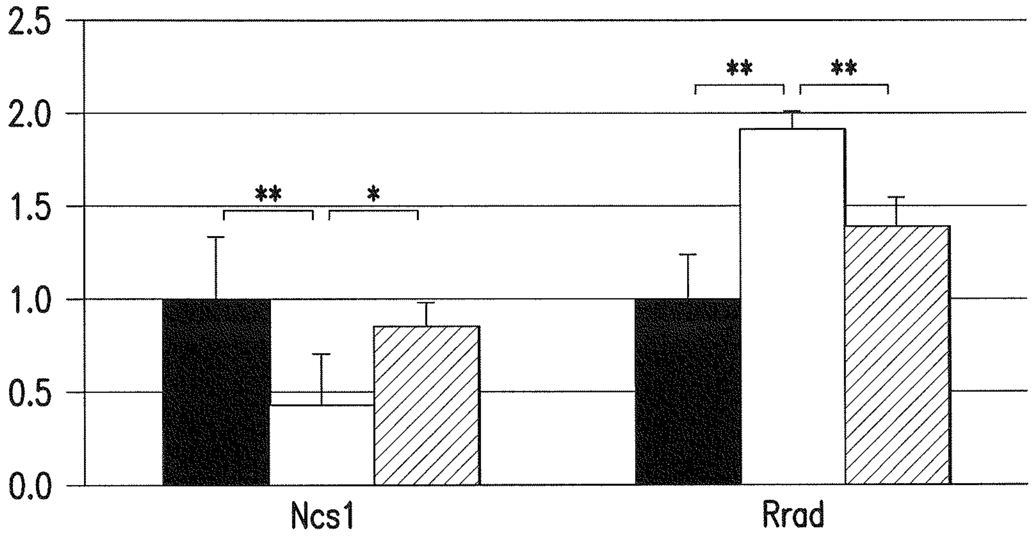
FIG. 11 shows that the intramuscular treatment of mice injected with HcTeTx affects the expression of genes related to the homeostasis of calcium in the spinal cord of transgenic SOD1G93A mice. The levels of expression were determined of genes Ncsl and Rrad in transgenic mice treated with HcTeTx (grey) or with the empty plasmid (white). The changes in levels of messenger RNA in the groups of rats above were compared to wild-type mice (black). (*P<0.05; the error bars show SEM; n=5 mice per group).
Figure 12A:
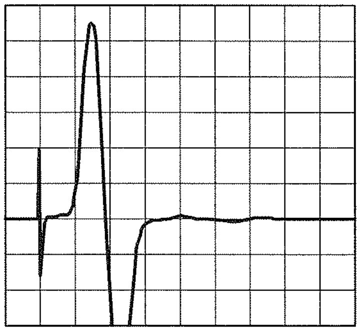
FIG. 12(A) shows recording from a wild-type mouse at 16 weeks of age.
Figure 12B:
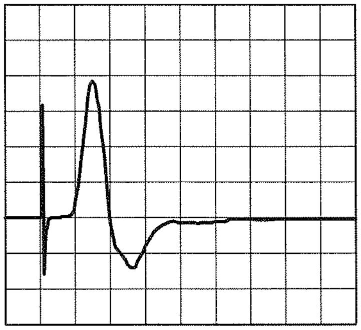
FIG. 12(B) shows recording from a SOD1G93A mouse at 12 weeks of age.
Figure 12C:
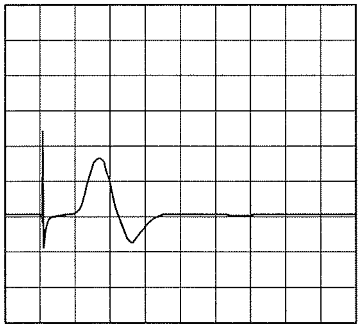
FIG. 12(C) shows recording from a SOD1G93A mouse at 16 weeks of age. Note the marked decline in amplitude and the slight increase in latency from the stimulus to the onset of the M wave in SOD1G93A mice, abnormalities that progress with time (compare FIG. 12(B) and FIG. 12(C)). Squares in the recording are 10 mV in height and 1 ms in width.
Figure 12D:
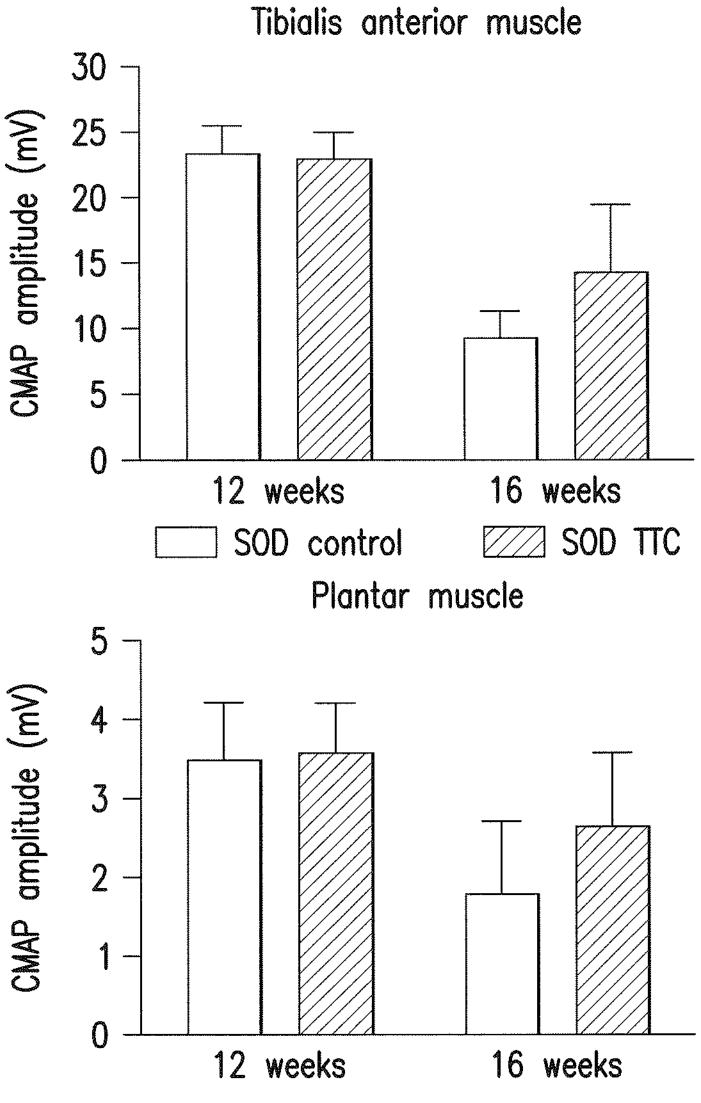
(FIG. 12(D)) Histogram of the mean CMAP (M wave) amplitude in tibialis anterior and plantar muscles in SOD1G93A mice. The amplitudes were similar in control (vehicle-plasmid mice) and HcTeTx-treated mice (SOD-TTC) at 12 weeks, but declined more markedly in control than in treated mice at 16 weeks. The neurophysiological results are shown on TABLE 3.

In the RT-PCR experiments it was found that the expression of the NCS1 gene was repressed (P<0.05) in the transgenic mice with late symptoms in relation to the wild-type mice of the same age. At the same time, the mice that received the intramuscular treatment with HcTeTx had higher levels of NCSI (P<0.05), approaching those of the wild type. With the same samples, the levels were measured of messenger RNA of the gene related to Ras and associated the diabetes gene (Rrad). This example shows that the levels of Rrad were increased almost twice in the spinal cord of the control transgenic mice when compared to wild-type mice of similar age. However, in comparison to the control mice, the treatment with HcTeTx in SOD1G93A mice perceptibly reduced the expression of Rrad (P<0.05), reaching similar values to those obtained in the wild-type mice (FIG. 11).

Example 5

In Vivo Comparative Efficiency Assay: HcTeTx Versus Riluzole in SOD1G93A Mice

Materials and Methods 1.1 Construction of Recombinant Plasmid Carrying HcTeTx DNA.

A HcTeTx-encoding gene is cloned into the pcDNA3.1 (Invitrogen S.A., Prat de Llobregat, Spain) eukaryotic expression plasmid under control of the cytomegalovirus (CMV) immediate-early promoter. The HcTeTx gene is removed from pGex-HcTeTx plasmid (Ciriza et al., 2008a) with BamHI and NodI restriction enzymes and inserted into pCMV to create the pCMV-HcTeTx plasmid. After sequencing, vectors are expanded in chemically competent *Escherichia coli* (DH5α) and purified using Genelute maxiprep-kit (Sigma-Aldrich Química, S.A., Madrid, Spain).

1.2 Extraction of the Polypeptide Consisting of the C-Terminal Domain of the Heavy Chain of the Tetanus Toxin (HcTeTx).

The HcTeTx polypeptide is obtained following the protocol described by Gil et al. (2003).

1.3 Transgenic Mice.

Transgenic mice with the G93A human SOD1 mutation (B6SJL-Tg[SOD1-G93A]1Gur) are purchased from The Jackson Laboratory (Bar Harbor, Me., USA). Hemizygotes are maintained by breeding SOD1G93A males with female littermates. The offspring is identified by PCR amplification of DNA extracted from the tail tissue, as described in The Jackson Laboratory protocol for genotyping hSOD1 transgenic mice (http://jaxmice.jax.org/pub-cgi/protocols.sh?objtype=protocol,protocol_id=523). Mice are housed in the Unidad Mixta de Investigación of the University of Zaragoza. Food and water are available ad libitum. All experimental procedures are approved by the Ethics Committees of our institutions and follow the international guidelines for the use of laboratory animals based on the guidelines for the preclinical in vivo evaluation of pharmacological active drugs for ALS/MND. A total of 240 mice, divided into 12 20-mice groups (10 male and 10 female in each group) are used.

1.4 Intramuscular Injection.

SOD1G93A transgenic mice are injected intramuscularly at eight weeks of age with 300 μg doses (1×) of pCMV-HcTeTx using an insulin syringe (25GA 5/8 Becton Dickinson SA, Madrid, Spain) into the quadriceps femoris muscles (two injections with 50 μg per muscle, total 200 μg) and triceps brachii muscles (one injection with 50 μg per muscle, total 100 μg) bilaterally. Also, 3000 μg doses (10×) and 30 μg doses (0.1×) are applied. Control group mice are similarly injected with the same amount of empty plasmid. pCMV-HcTeTx is administered as a single dose. In case of the protein, SOD1G93A transgenic mice is injected with 250 μl at a concentration of 0.5 μM of the polypeptide that includes the C-Terminal Domain of the tetanus toxin (HcTeTx) (1× dose). Also, 0.1× doses (0.05 μM) and 10× doses (5 μM) are administered, as well as controls (injection without polypeptide). The injections are repeated weekly throughout the mice's entire lives. Riluzole at a concentration of 100 micrograms/ml is administered in water, three times, with weekly changes.

1.5 Rotarod, Hanging-Wire Test, and Survival.

The hanging wire test is used to assess muscular strength and onset of ALS symptoms. Animals perform this test weekly beginning at eight weeks of age. Each mouse is given up to three attempts to hold on to the inverted lid for a maximum of 180 s, and the longest period is recorded. The rotarod test is used to assess motor coordination, strength, and balance. Mice are trained for one week to perform on an accelerating rotarod (ROTA-ROD/RS, LE8200, LSI-LETICA Scientific Instruments; Panlab, Barcelona, Spain). Baseline performance is measured at eight weeks of age and tested weekly thereafter. Disease endpoint is defined as the day on which the mice are unable to right themselves within 30 s when placed on their sides (late symptomatic stage of the disease).

Mice treated mice with naked DNA encoding HcTeTx or the HcTeTx polypeptide show (i) a delay in the start of symptoms, (ii) improvement of motor activity, and (iii) postponement of the end point of the disease, which favorably compare to the effects observed after treatment with Riluzole.

Example 6

Protective Effect of HcTeTxC on the Neuromuscular Function of SOD1G93A Mice

Materials and Methods 1.1 Construction of Recombinant Plasmid Carrying HcTeTx DNA.

A HcTeTx-encoding gene was cloned into the pcDNA3.1 (Invitrogen S.A., Prat de Llobregat, Spain) eukaryotic expression plasmid under control of the cytomegalovirus (CMV) immediate-early promoter. The HcTeTx gene was removed from pGex-HcTeTx plasmid (Ciriza et al., 2008) with BamHI and NotI restriction enzymes and inserted into pCMV to create the pCMV-HcTeTx plasmid. After sequencing, vectors were expanded in chemically competent *Escherichia coli* (DH5α) and purified using Genelute maxiprep-kit (Sigma-Aldrich Química, S.A., Madrid, Spain).

1.2 Transgenic Mice.

Transgenic mice with the G93A human SOD1 mutation (B6SJL-Tg[SOD1-G93A]1Gur) were purchased from The Jackson Laboratory (Bar Harbor, Me., USA). Hemizygotes were maintained by breeding SOD1G93A males with female littermates. The offspring were identified by PCR amplification of DNA extracted from the tail tissue, as described in The Jackson Laboratory protocol for genotyping hSOD1 transgenic mice (http://jaxmice.jax.org/pub-cgi/protocols.sh?objtype=protocol,protocol_id=523). Mice were housed in the Unidad Mixta de Investigación of the University of Zaragoza. Food and water were available ad libitum. All experimental procedures were approved by the Ethics Committees of the institutions and followed the international guidelines for the use of laboratory animals based on the guidelines for the preclinical in vivo evaluation of pharmacological active drugs for ALS/MND.

1.3 Electrophysiological Tests.

Two groups of male SOD1G93A mice were injected with recombinant plasmid pCMV-HcTeTx or empty plasmid in the hindpaw. To assess neuromuscular function, nerve conduction tests were performed at 12 and 16 weeks of age. A third group of age-matched wild-type mice (n=8) was also tested for comparisons. For motor nerve conduction tests, the sciatic nerve was stimulated percutaneously with a pair of needle electrodes placed near the sciatic notch, and the compound muscle action potential (CMAP, M wave) was recorded from tibialis anterior and plantar muscles with microneedle electrodes.

For sensory nerve conduction tests, the recording electrodes were placed near the digital nerves of the fourth toe to record the compound sensory nerve action potential (CNAP). The evoked potentials were amplified and displayed on a digital oscilloscope (Tektronix 450S) at appropriate settings to measure the amplitude from baseline to the maximal negative peak and the latency from stimulus to the onset of the first negative deflection (Navarro et al., 1994; Verdu & Buti, 1994; Udina et al., 2004). During 7 electrophysiological tests, the animals were placed over a warm flat steamer controlled by a water circulating pump to maintain body temperature.

Results

The neuromuscular function of SOD1G93A mice was assessed at two time points: at 12 weeks of age, just before the approximate time of disease onset, and 16 weeks of age, when the disease is in a late symptomatic stage. By 12 weeks of age, there were marked abnormalities in motor nerve conduction tests, evidenced by a 40%-50% decline in the amplitude of the M waves in tibialis anterior and plantar muscles of both HcTETX-treated and vehicle-plasmid transgenic mice (FIG. 12, TABLE 3).

TABLE 3 shows neurophysiological results in the groups of wild-type (WT), SOD1G93A control (SOD control), and SOD1G93A HcTeTx-treated (SOD+HcTeTx) mice. Values are mean±SEM

| | | 12 weeks | | | 16 weeks | | |
|---|---|---|---|---|---|---|---|
| | Group (n) | WT (8) | SOD control (7) | SOD + TTC (7) | WT (8) | SOD control (5) | SOD + TTC (5) |
| Tibialis ant | Latency (ms) | 0.94 ± 0.04 | 1.09 ± 0.04 * | 1.09 ± 0.02 * | 0.87 ± 0.03 | 1.13 ± 0.04 * | 1.14 ± 0.04 * |
| muscle | CMAP (mV) | 52.3 ± 2.4 | 23.4 ± 2.2 * | 23.0 ± 2.0 * | 50.4 ± 2.8 | 9.2 ± 2.1 * | 14.3 ± 5.2 * |
| Plantar | Latency (ms) | 1.69 ± 0.04 | 1.92 ± 0.03 * | 1.94 ± 0.07 * | 1.55 ± 0.08 | 2.00 ± 0.10 * | 2.23 ± 0.18 * |
| muscle | CMAP (mV) | 7.2 ± 0.4 | 3.5 ± 0.7 * | 3.6 ± 0.6 * | 7.0 ± 0.5 | 1.8 ± 0.9 * | 2.6 ± 0.9 * |
| Digital | Latency (ms) | 1.08 ± 0.03 | 1.26 ± 0.06 * | 1.17 ± 0.05 | 1.00 ± 0.06 | 1.24 ± 0.05 * | 1.21 ± 0.04 |
| nerve | CNAP (μV) | 51.7 ± 3.7 | 43.9 ± 5.8 | 41.2 ± 4.2 | 51.4 ± 3.5 | 44.6 ± 6.6 | 41.0 ± 5.4 |

* $P < 0.05$ vs. WT group.
CMAP, compound muscle action potential; CNAP, compound nerve action potential.

There was also a slight but significant increase in the latency (about 14% longer) compared to age-matched wild-type mice (TABLE 3). At 16 weeks, there was a clear reduction in the M wave amplitudes in vehicle-treated SOD mice, to about 20%-25% of normal values (FIG. 12). This decline was less pronounced in HcTeTx-treated mice (to 30%-38%), although the differences did not attain significance. The latency of M wave onset slightly increased between 12 and 16 weeks in the vehicle-treated SOD1G93A mice (TABLE 3), in contrast to the mild shortening and consequent increase in conduction velocity that occur in normal mice during this age (Verdu et al., 1996).

Fibrillation potentials were detected with moderate abundance in the tested muscles at 12 weeks; these were increased at 16 weeks. In contrast to motor nerve abnormalities, sensory nerve conduction tests showed no significant differences in the amplitude of CNAPs recorded from the digital nerves in the toes between groups (TABLE 3). The latency time of sensory CNAP was slightly delayed in vehicle-plasmid SOD1G93A mice compared to age-matched wild-type animals. These findings indicate that gene delivery of HcTeTX has protective effects on the ALS murine model expressing the G93A mutant human SOD1 gene with regard to neuromuscular function.

Example 7

HcTeTx Protects Against Spinal Motor Neuron Loss in SOD1G93A Mice and Promotes a Reduction of Microgliosis Materials and Methods 1.1 Construction of Recombinant Plasmid Carrying HcTeTx DNA.

A HcTeTx-encoding gene was cloned into the pcDNA3.1 (Invitrogen S.A., Prat de Llobregat, Spain) eukaryotic expression plasmid under control of the cytomegalovirus (CMV) immediate-early promoter. The HcTeTx gene was removed from pGex-HcTeTx plasmid (Ciriza et al., 2008a) with BamHI and NotI restriction enzymes and inserted into pCMV to create the pCMV-HcTeTx plasmid. After sequencing, vectors were expanded in chemically competent *Escherichia coli* (DH5α) and purified using Genelute maxiprep-kit (Sigma-Aldrich Química, S.A., Madrid, Spain).

1.2 Transgenic Mice.

Transgenic mice with the G93A human SOD1 mutation (B6SJL-Tg[SOD1-G93A]1Gur) were purchased from The Jackson Laboratory (Bar Harbor, Me., USA). Hemizygotes were maintained by breeding SOD1G93A males with female littermates. The offspring were identified by PCR amplification of DNA extracted from the tail tissue, as described in The Jackson Laboratory protocol for genotyping hSOD1 transgenic mice (http://jaxmice.jax.org/pub-cgi/protocols.sh?objtype=protocol,protocol_id=523). Mice were housed in the Unidad Mixta de Investigación of the University of Zaragoza. Food and water were available ad libitum. All experimental procedures were approved by the Ethics Committees of the institutions and followed the international guidelines for the use of laboratory animals based on the guidelines for the preclinical in vivo evaluation of pharmacological active drugs for ALS/MND.

1.3 Histological and Immunohistochemical Processing.

Male SOD1G93A mice were injected with recombinant plasmid pCMV-HcTeTx or empty plasmid in the hindpaw. To assess neuromuscular function, nerve conduction tests were performed at 16 weeks of age. Following electrophysiological tests, the animals (n=5) were perfused with 4% paraformaldehyde in PBS. The lumbar segment of the spinal cord was removed, post-fixed for 24 h, and cryopreserved in 30% sucrose. Transverse 40 μm thick sections were serially cut with a cryotome (Thermo Electron, Cheshire, UK), at L2, L3 and L4 segmental levels.

For each segment, each section of a series of 10 was collected sequentially on separate gelatin-coated slides. One slide was rehydrated for 1 min with tap water and stained for 1 h with an acidified solution of 3.1 mM cresyl violet. Then, the slides were washed in distilled water for 1 min, dehydrated, and mounted with DPX (Fluka). Motor neurons were identified by their localization in the lateral ventral horn of the stained spinal cord sections and counted following strict size and morphological criteria.

Overlapping images covering the whole lateral ventral horn were taken at 40×, and a 20 μm squared grid was superimposed onto each micrograph. Only motor neurons with diameters larger than 20 μm and with polygonal shape and prominent nucleoli were counted. The number of motor neurons present in both ventral horns was counted in four serial sections of each L2, L3 and L4 segments. Another series of sections was blocked with TBS-Triton-FBS and incubated for 2 days at 4° C. with primary antibody anti-glial fibrilar acidic protein (GFAP, 1:1000, Dako) or rabbit anti-ionized calcium binding adaptor molecule 1 (Iba1, 1:2000, Wako) to label astrocytes and microglia respectively.

After washes, sections were incubated for 1 day at 4° C. Cy3-conjugated secondary:antibody (1:200; Jackson Immunoresearch). Sections from the three groups of mice were processed in parallel for immunohistochemistry. Microphotographs of the grey matter of the ventral horn were taken at 400× and, after defining the threshold for background correction, the integrated density of GFAP or Iba1 labeling was measured using ImageJ software (Penas et al., 2009). The integrated density is the area above the threshold for the mean density minus the background.

Results

Figure 13A:
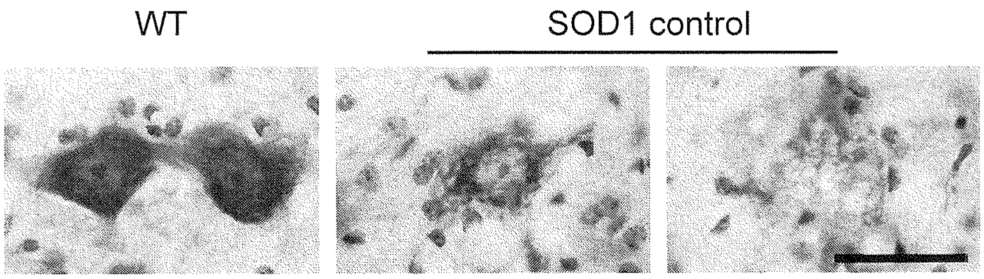
FIG. 13(A) shows microphotographs of MNs from wild type and SOD mice stained with cresyl violet. Note the vacuolization and disintegration of Nissl substance in the SOD1G93A MNs. Bar=40 μm.

The degenerative events underwent by SOD1G93A mice motor neurons were observed under light microscopy. A prominent feature of the motor neurons in SOD1G93A mice was a vacuolization of the cytoplasm indicating active degeneration (FIG. 13(A)). These vacuoles had different sizes and a clear content. SOD1G93A mice motor neurons also showed a depletion of Nissl substance, becoming pale and less visible. In contrast, the motor neurons in wild type mice had darkly stained aggregates of Nissl substance and no cytoplasmic vacuoles (FIG. 13(A)). The extent of motor neurons degeneration was determined by counting the number of stained motor neurons in the lateral ventral horns of lumbar spinal cord sections of wild type and SOD1G93A mice at 16 weeks of age.

Figure 13B:
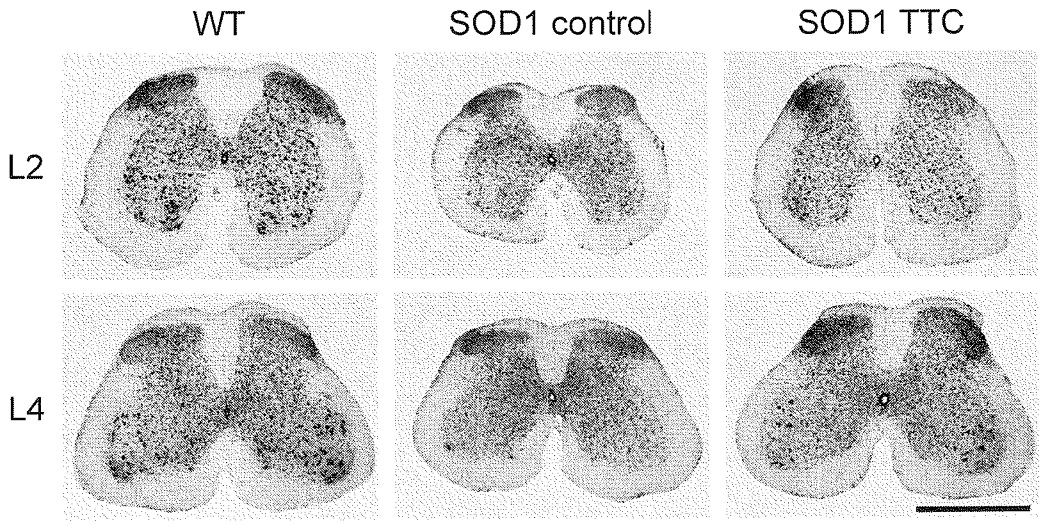
FIG. 13(B) shows representative micrographs showing cross-sections of the lumbar spinal cords stained with cresyl violet from a wild type, a control SOD1G93A and a SOD 1G93A-HcTeTx (SOD-TTC) treated mouse at 16 weeks of age. Bar=500 μm.
Figure 13C:
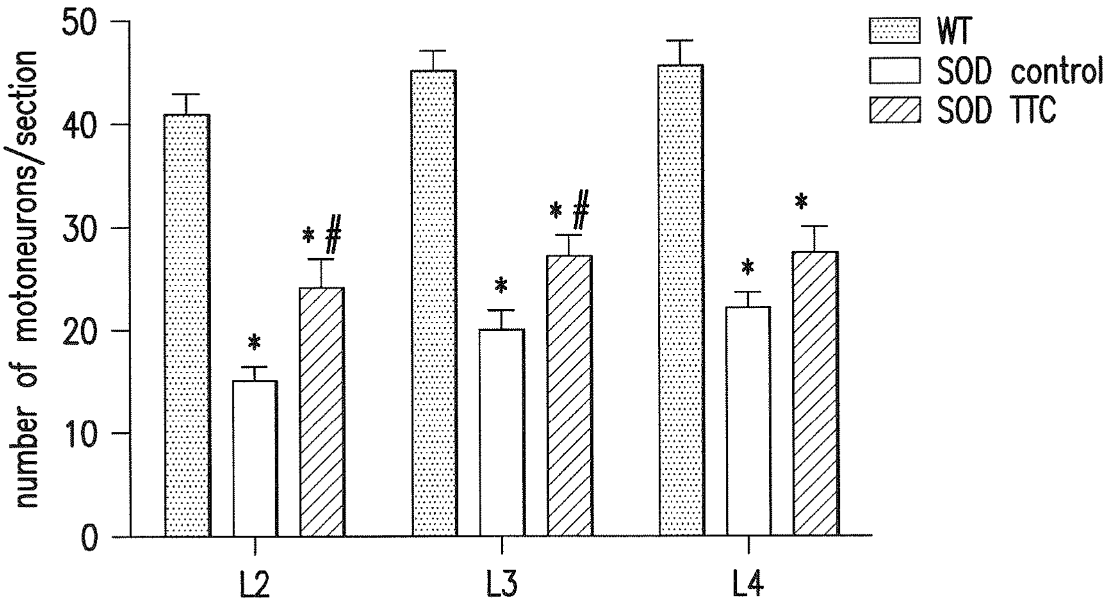
FIG. 13(C) shows motor neuron survival assessed by counting the number of stained (cresyl violet) MNs within the lateral column of each ventral horn. The results show the average numbers of MNs counted in the ventral horns at L2, L3 and L4 spinal cord segments of wild type, control SOD1G93A (vehicle-plasmid mice) and HcTeTx-treated SOD mice (SOD-TTC) (n=5 per group). *P<0.05 vs. wild type; #P<0.05 vs. control SOD1.

The three lumbar segments sectioned contain motor nuclei of different muscles of the hindlimbs; the nuclei of quadriceps femoris muscles, in which plasmid injections were made at 8 weeks, are mainly located at L2; whereas motor nuclei of tibialis anterior and foot plantar muscles, that were tested electrophysiologically, are mostly represented at L3 and L4 levels respectively (McHanwell & Biscoe, 1981). FIG. 13(B) shows representative spinal cord sections from wild type, control SOD1G93A mice, and SOD1G93A-HcTeTx treated mice. Only neurons that met the criteria of a motor neuron were included in the counts. Small neurons were excluded from our counts; even if these neurons were, in fact, atrophic motor neurons they were unlikely to be functional motor neurons. The number of surviving motor neurons was significantly reduced at the lumbar spinal cord in both SOD1G93A groups compared to the wild-type age matched controls (FIG. 13(C)).

Nevertheless, the extent of motor neuron loss was significantly higher in vehicle-plasmid injected (about 43% of surviving motor neuron with respect to wild type mice) than in HcTeTx-treated SOD1G93A mice (about 60%). The results indicate that the neuroprotective effect of HcTeTx extended along spinal cord segments and not only affected the segment containing the quadriceps muscle motoneuronal pool. However, the improvement in motor neurons survival induced by HcTeTx showed a slight gradient, since the proportion of motor neurons was increased in mice treated with HcTeTx about 22% at L2, 16% at L3, and 12% at L4 compared with SOD1G93A control mice (FIG. 13(C)).

Figure 14A:
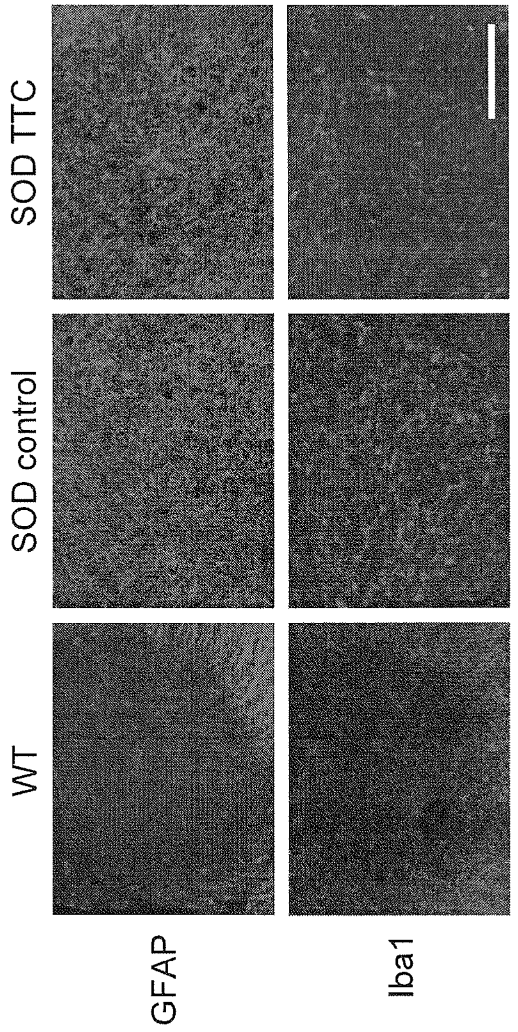
FIG. 14(A) shows representative microphotographs of spinal cords ventral horns from a wild type, a SOD1G93A and a SOD1G93A-HcTeTx (SOD-TTC) treated mice immunolabeled with markers for astrocytes (GFAP) and microglia (Iba1). Bar=100 μm.
Figure 14B:
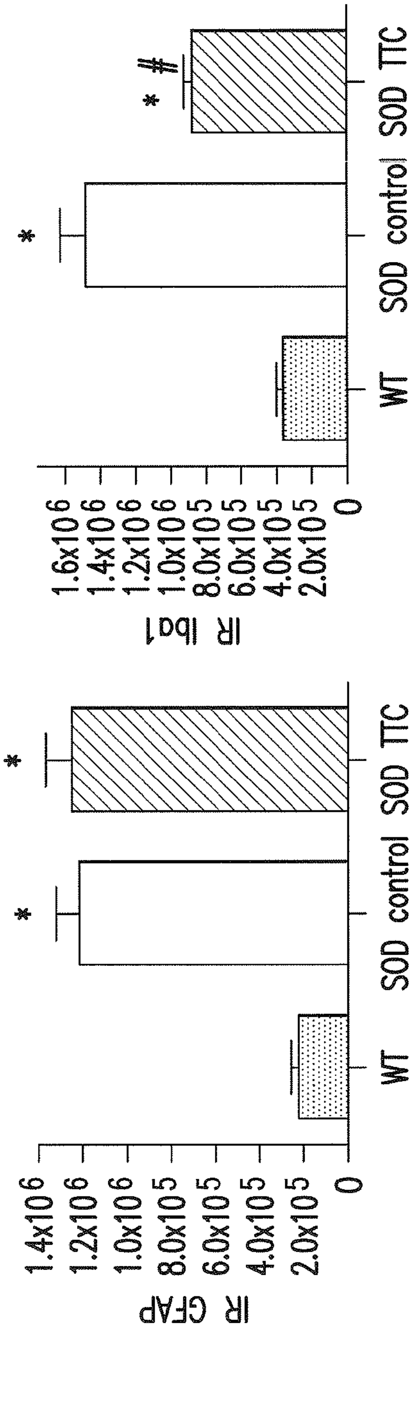
FIG. 14(B) shows histograms representing the quantification of GFAP and Iba1 immunoreactivity (IR) in the three groups of mice. *P<0.05 vs. wild type; #P<0.05 vs. control SOD1.
Figure 15:
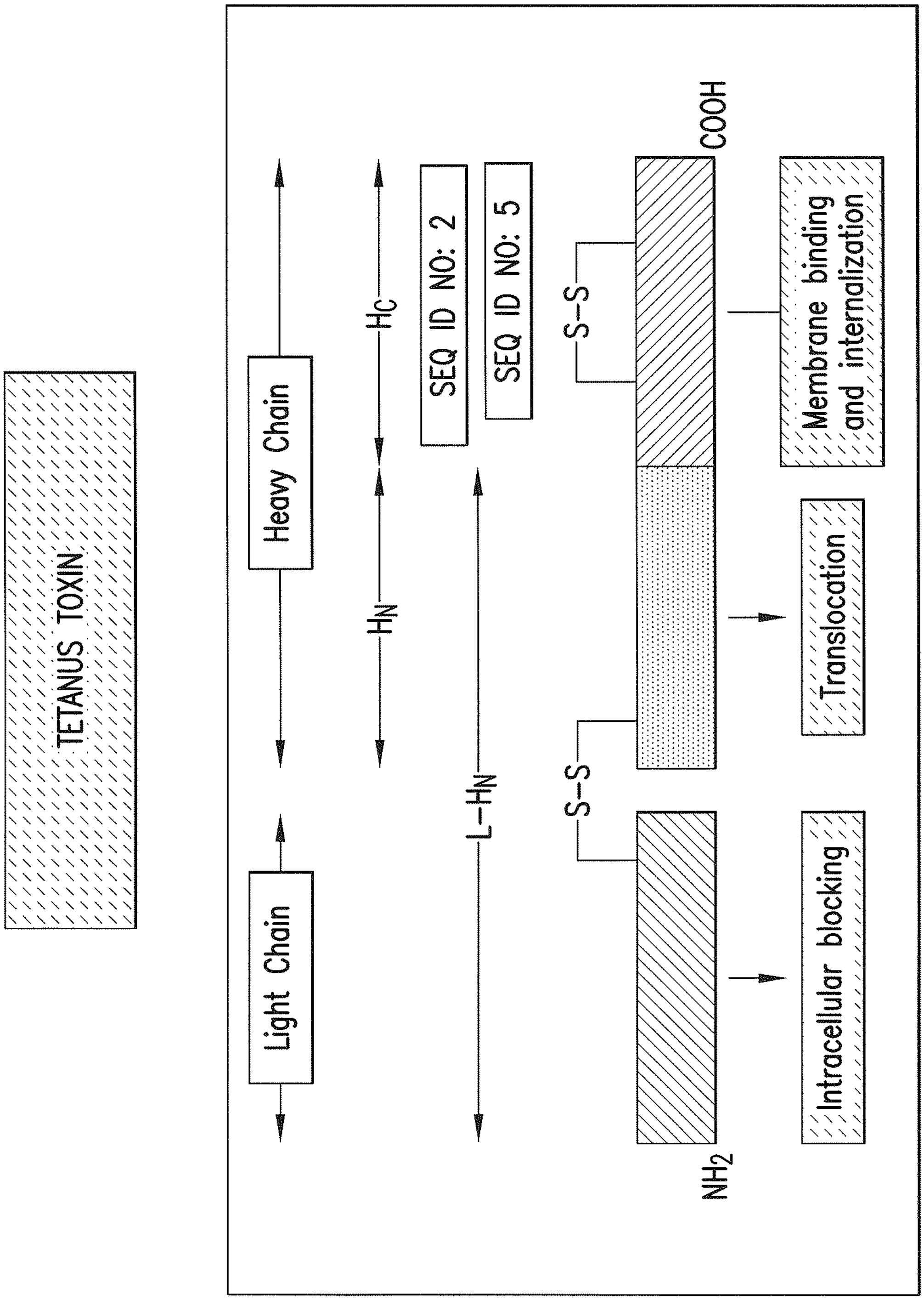
FIG. 15 presents a schematic representation of the domain structure of the tetanus toxin precursor protein, showing the locations of the Heavy Chain and Light Chain and their respective functional roles. Also shown are the relative locations of SEQ ID NO: 2 and SEQ ID NO: 5 with the C-terminal region of the Heavy Chain.

In order to indirectly examine the state of lumbar motor neurons and the reactive glial response, we stained the spinal cord sections with markers for astrocytes (GFAP) or microglia (Iba1). Glial reactivity was measured in L2 sections, as this segment had the highest increased proportion of motor neuron survival. Reactive astrocytosis and microgliosis were clearly evident in both SOD1G93A groups, at significantly higher levels than in wild type mice, which had a lower basal labelling for these markers (FIG. 14(A)). Quantitative analysis of the immunoreactivity showed that the HcTeTx treatment had no effect on astrocyte reactivity, whereas it was able to promote a significant reduction of the increased microglia reactivity in the SOD1G93A mice (FIG. 14(B)).

REFERENCES

Brown. R. H. Jr. "Amyotrophic lateral sclerosis. Insights from genetics," *Arch. Neurol*., Vol. 54(10): 1246-1250 (1997).

Ciriza, J., Moreno-Igoa, M., Calvo, A. C, Yague, G., Palacio, J., Miana-Mena, F. J., Muñoz, M. J., Zaragoza, P., Brulet, P., and Osta, R. "A Genetic fusion GDNF-C fragment of tetanus toxin prolongs survival in a symptomatic mouse ALS model," *Restorative Neurology and Neuroscience*, Vol. 26(6): 459-65 (2008b).

Ciriza, J; Martín-Burriel, I, García Ojeda M. E., Agulhon, C, Miana-Mena, F. J., Muñoz, M. J., Zaragoza, P., Brûlet, P., and Osta, R. "Antiapototic activity maintenance of Brain Derived Neurotrophic factor and the C fragment of the tetanus toxin fusion protein." *Cent. Eur. J. Biol*., Vol. 3(2): 105-112 (2008a).

Francis, J. W., Bastia, E., Matthews, C. C., Parks, D. A., Schwarzschild, M. A., Brown, R. H. Jr, and Fishman, P. S. "Tetanus toxin fragment C as a vector to enhance delivery of proteins to the CNS," *Brain Res*., Vol. 1011(1): 7-13 (2004).

Gil, C., ChalB-Oukadour, I., and Aguilera, J., "C-terminal fragment of tetanus toxin heavy chain activates Akt and MEK/ERK signalling pathways in a Trk receptor-dependent manner in cultured cortical neurons," *Biochem. J*., Vol. 373: 613-620 (2003).

Gurney, M. E., Pu, H., Chiu, A. Y., Dal Canto, M. C., Polchow, C. Y., Alexander, D. D., Caliendo, J, Hentati, A., Kwon, Y. W., Deng, H. X., et al. "Motor neuron degeneration in mice that express a human Cu, Zn superoxide dismutase mutation," *Science*, Vol. 264 (5166): 1772-5 (1994).

Haase, G., Pettmann, B., Bordet, T., Villa, P., Vigne, E., Schmalbruch, H., and Kahn, A. "Therapeutic benefit of ciliary neurotrophic factor in progressive motor neuronopathy depends on the route of delivery," *Ann. Neurol*., Vol. 45(3): 296-304 (1999).

McFerran, B. W., Graham, M. E., and Burgoyne, R. D. "Neuronal Ca2+ sensor 1, the mammalian homologue of frequenin, is expressed in chromaffin and PC12 cells and regulates neurosecretion from dense-core granules," *J. Biol. Chem., Vol.* 273: 22768-22772 (1998).

McHanwell, S., and Biscoe, T. J. "The localization of motoneurons supplying the hindlimb muscles of the mouse," *Philos. Trans. R. Soc. Lond. B Biol. Sci*., Vol. 293: 477-508 (1981).

Navarro, X., Verdu, E., and Buti, M. "Comparison of regenerative and reinnervating capabilities of different functional types of nerve fibers." *Exp. Neurol*., Vol. 129: 217-224 (1994).

Penas, C., Casas, C., Robert, I., Forés, J., and Navarro, X. "Cytoskeletal and activity related changes in spinal motoneurons after root avulsion," *J. Neurotrauma*, Vol. 26: 763-779 (2009).

Sakowski, S. A., Schuyler, A. D., and Feldman, E. L. "Insulin-like growth factor-I for the treatment of amyotrophic lateral sclerosis." *Amyotroph. Lateral Scler., Vol.* 10(2): 63-73 (2009).

Schaad, N. C., De Castro, E., Nef, S., Hegi, S., Hinrichsen, R., Martone, M. E., Ellisman, M. H., Sikkink, R., Rusnak, F., Sygush, J., and Nef, P. "Direct modulation of calmodulin targets by the neuronal calcium sensor NCS-1," *Proc. Natl. Acad. Sci. USA*, Vol. 93: 9253-9258 (1996).

Tu, P. H., Raju, P., Robinson, K. A., Gurney, M. E., Trojanowski, J. Q., and Lee V. M. "Transgenic mice carrying a human mutant superoxide dismutase transgene develop neuronal cytoskeletal pathology resembling human amyotrophic lateral sclerosis lesions," *Proc. Natl. Acad. Sci. USA*., Vol. 93(7): 3155-3160 (1996).

Udina, E., Rodriguez, F. J., Verdu, E., Espejo, M., Gold, B. G., and Navarro, X. "FK506 enhances regeneration of axons across long peripheral nerve gaps repaired with collagen guides seeded with allogeneic Schwann cells," *Glia*, Vol. 47: 120-129 (2004).

Verdu, E., Buti, M., and Navarro, X. "Functional changes of the peripheral nervous system with aging in the mouse." *Neurobiol. Aging*, Vol. 17: 73-77 (1996).

Verdu, E, and. Buti M. "Comparison of regenerative and reinnervating capabilities of different functional types of nerve fibers," *Exp Neurol* 129: 217-224 (1994).

All publications such a textbooks, journal articles, Genbank or other sequence database entries, published applications and patent applications mentioned in this specification are herein incorporated by reference to the same extent as if each individual publication or patent was specifically and individually indicated to be incorporated by reference.

What is claimed is:

1. A method for ameliorating the symptoms of motor neuron degeneration in a subject with Amyotrophic Lateral Sclerosis (ALS), comprising administering a polypeptide comprising the carboxy-terminal domain of the heavy subunit of the tetanus toxin (HcTeTx) to said subject, wherein:

(i) the polypeptide comprises the sequence of SEQ ID NO:2 or SEQ ID NO:5 or a fragment thereof;

(ii) the polypeptide increases the survival of transgenic SOD 1093A mice; and, (iii) the polypeptide is not a targeting moiety for another therapeutic molecule.

2. The method of claim 1, wherein said polypeptide comprising the carboxy-terminal domain of the heavy subunit of the tetanus toxin (HcTeTx) is SEQ ID NO: 2.

3. The method of claim 1 where said polypeptide comprising the carboxy-terminal domain of the heavy subunit of the tetanus toxin (HcTeTx) is SEQ ID NO: 5.

4. The method of claim 1, wherein said polypeptide is administered orally, parenterally, intramuscularly, or nasally.

5. The method of claim 1, wherein said polypeptide is administered intraperitoneally.

6. The method of claim 1, wherein said method is performed in vivo in a mammal.

7. The method according to claim 1, wherein said polypeptide has neuroprotectant activity.

8. A method for ameliorating the symptoms of motor neuron degeneration in a subject with Amyotrophic Lateral Sclerosis (ALS), comprising administering a polypeptide consisting essentially of the carboxy-terminal domain of the heavy subunit of the tetanus toxin (HcTeTx) to said subject, wherein:

(i) the polypeptide comprises the sequence of SEQ ID NO:2 or SEQ ID NO:5 or a fragment thereof;

(ii) the polypeptide increases the survival of transgenic SOD1G93A mice; and, (iii) the polypeptide is not a targeting moiety for another therapeutic molecule.

9. A method for ameliorating the symptoms of motor neuron degeneration in a subject with Amyotrophic Lateral Sclerosis (ALS), comprising administering a polypeptide comprising the carboxy-terminal domain of the heavy subunit of the tetanus toxin (HcTeTx), wherein:

(i) the polypeptide consists of SEQ ID NO: 2 or SEQ ID NO: 5;

(ii) the polypeptide increases the survival of transgenic SOD1G93A mice; and, (iii) polypeptide is not a targeting moiety for another therapeutic molecule.

* * * * *

SEQUENCE LISTING

```
<160> NUMBER OF SEQ ID NOS: 6

<210> SEQ ID NO 1
<211> LENGTH: 1392
<212> TYPE: DNA
<213> ORGANISM: Clostridium tetani

<400> SEQUENCE: 1

atggtttttt caacaccaat tccattttct tattctaaaa atctggattg ttgggttgat      60

aatgaagaag atatagatgt tatattaaaa aagagtacaa ttttaaattt agatattaat     120

aatgatatta tatcagatat atctgggttt aattcatctg taataacata tccagatgct     180

caattggtgc ccggaataaa tggcaaagca atacatttag taaacaatga atcttctgaa     240
```

```
gttatagtgc ataaagctat ggatattgaa tataatgata tgtttaataa ttttaccgtt    300
agcttttggt tgagggttcc taaagtatct gctagtcatt tagaacaata tggcacaaat    360
gagtattcaa taattagctc tatgaaaaaa catagtctat caataggatc tggttggagt    420
gtatcactta aaggtaataa cttaatatgg actttaaaag attccgcggg agaagttaga    480
caaataactt ttagggattt acctgataaa tttaatgctt atttagcaaa taaatgggtt    540
tttataacta ttactaatga tagattatct tctgctaatt tgtatataaa tggagtactt    600
atgggaagtg cagaaattac tggtttagga gctattagag aggataataa tataacatta    660
aaactagata gatgtaataa taataatcaa tacgtttcta ttgataaatt taggatattt    720
tgcaaagcat taaatccaaa agagattgaa aaattataca caagttattt atctataacc    780
tttttaagag acttctgggg aaaccccttta cgatatgata cagaatatta tttaatacca    840
gtagcttcta gttctaaaga tgttcaattg aaaaatataa cagattatat gtatttgaca    900
aatgcgccat cgtatactaa cggaaaattg aatatatatt atagaaggtt atataatgga    960
ctaaaattta ttataaaaag atatacacct aataatgaaa tagattcttt tgttaaatca   1020
ggtgatttta ttaaattata tgtatcatat aacaataatg agcacattgt aggttatccg   1080
aaagatggaa atgcctttaa taatcttgat agaattctaa gagtaggtta taatgcccca   1140
ggtatccctc tttataaaaa aatggaagca gtaaaattgc gtgatttaaa aacctattct   1200
gtacaactta aattatatga tgataaaaat gcatctttag gactagtagg tacccataat   1260
ggtcaaatag gcaacgatcc aaatagggat atattaattg caagcaactg gtactttaat   1320
catttaaaag ataaaatttt aggatgtgat tggtactttg tacctacaga tgaaggatgg   1380
acaaatgatt aa                                                         1392
```

```
<210> SEQ ID NO 2
<211> LENGTH: 462
<212> TYPE: PRT
<213> ORGANISM: Clostridium tetani

<400> SEQUENCE: 2

Val Phe Ser Thr Pro Ile Pro Phe Ser Tyr Ser Lys Asn Leu Asp Cys
1               5                   10                  15

Trp Val Asp Asn Glu Glu Asp Ile Asp Val Ile Leu Lys Lys Ser Thr
            20                  25                  30

Ile Leu Asn Leu Asp Ile Asn Asn Asp Ile Ile Ser Asp Ile Ser Gly
        35                  40                  45

Phe Asn Ser Ser Val Ile Thr Tyr Pro Asp Ala Gln Leu Val Pro Gly
    50                  55                  60

Ile Asn Gly Lys Ala Ile His Leu Val Asn Asn Glu Ser Ser Glu Val
65                  70                  75                  80

Ile Val His Lys Ala Met Asp Ile Glu Tyr Asn Asp Met Phe Asn Asn
                85                  90                  95

Phe Thr Val Ser Phe Trp Leu Arg Val Pro Lys Val Ser Ala Ser His
            100                 105                 110

Leu Glu Gln Tyr Gly Thr Asn Glu Tyr Ser Ile Ile Ser Ser Met Lys
        115                 120                 125

Lys His Ser Leu Ser Ile Gly Ser Gly Trp Ser Val Ser Leu Lys Gly
    130                 135                 140

Asn Asn Leu Ile Trp Thr Leu Lys Asp Ser Ala Gly Glu Val Arg Gln
145                 150                 155                 160
```

-continued

```
Ile Thr Phe Arg Asp Leu Pro Asp Lys Phe Asn Ala Tyr Leu Ala Asn
                165                 170                 175

Lys Trp Val Phe Ile Thr Ile Thr Asn Asp Arg Leu Ser Ser Ala Asn
            180                 185                 190

Leu Tyr Ile Asn Gly Val Leu Met Gly Ser Ala Glu Ile Thr Gly Leu
        195                 200                 205

Gly Ala Ile Arg Glu Asp Asn Asn Ile Thr Leu Lys Leu Asp Arg Cys
    210                 215                 220

Asn Asn Asn Asn Gln Tyr Val Ser Ile Asp Lys Phe Arg Ile Phe Cys
225                 230                 235                 240

Lys Ala Leu Asn Pro Lys Glu Ile Glu Lys Leu Tyr Thr Ser Tyr Leu
                245                 250                 255

Ser Ile Thr Phe Leu Arg Asp Phe Trp Gly Asn Pro Leu Arg Tyr Asp
            260                 265                 270

Thr Glu Tyr Tyr Leu Ile Pro Val Ala Ser Ser Ser Lys Asp Val Gln
        275                 280                 285

Leu Lys Asn Ile Thr Asp Tyr Met Tyr Leu Thr Asn Ala Pro Ser Tyr
    290                 295                 300

Thr Asn Gly Lys Leu Asn Ile Tyr Tyr Arg Arg Leu Tyr Asn Gly Leu
305                 310                 315                 320

Lys Phe Ile Ile Lys Arg Tyr Thr Pro Asn Asn Glu Ile Asp Ser Phe
                325                 330                 335

Val Lys Ser Gly Asp Phe Ile Lys Leu Tyr Val Ser Tyr Asn Asn Asn
            340                 345                 350

Glu His Ile Val Gly Tyr Pro Lys Asp Gly Asn Ala Phe Asn Asn Leu
        355                 360                 365

Asp Arg Ile Leu Arg Val Gly Tyr Asn Ala Pro Gly Ile Pro Leu Tyr
    370                 375                 380

Lys Lys Met Glu Ala Val Lys Leu Arg Asp Leu Lys Thr Tyr Ser Val
385                 390                 395                 400

Gln Leu Lys Leu Tyr Asp Asp Lys Asn Ala Ser Leu Gly Leu Val Gly
                405                 410                 415

Thr His Asn Gly Gln Ile Gly Asn Asp Pro Asn Arg Asp Ile Leu Ile
            420                 425                 430

Ala Ser Asn Trp Tyr Phe Asn His Leu Lys Asp Lys Ile Leu Gly Cys
        435                 440                 445

Asp Trp Tyr Phe Val Pro Thr Asp Glu Gly Trp Thr Asn Asp
    450                 455                 460
```

<210> SEQ ID NO 3
<211> LENGTH: 21
<212> TYPE: DNA
<213> ORGANISM: Artificial Sequence
<220> FEATURE:
<223> OTHER INFORMATION: (Primer)

<400> SEQUENCE: 3
agattccgcg ggagaagtta g 21

<210> SEQ ID NO 4
<211> LENGTH: 21
<212> TYPE: DNA
<213> ORGANISM: Artificial Sequence
<220> FEATURE:
<223> OTHER INFORMATION: (Primer)

<400> SEQUENCE: 4

-continued

```
tcgtaaaggg tttccccaga a                                                21


<210> SEQ ID NO 5
<211> LENGTH: 451
<212> TYPE: PRT
<213> ORGANISM: Clostridium tetani
<220> FEATURE:
<221> NAME/KEY: MISC_FEATURE
<222> LOCATION: (1)...(451)
<223> OTHER INFORMATION: Fragment of SEQ ID NO:2

<400> SEQUENCE: 5

Lys Asn Leu Asp Cys Trp Val Asp Asn Glu Glu Asp Ile Asp Val Ile
1               5                   10                  15

Leu Lys Lys Ser Thr Ile Leu Asn Leu Asp Ile Asn Asn Asp Ile Ile
            20                  25                  30

Ser Asp Ile Ser Gly Phe Asn Ser Ser Val Ile Thr Tyr Pro Asp Ala
        35                  40                  45

Gln Leu Val Pro Gly Ile Asn Gly Lys Ala Ile His Leu Val Asn Asn
    50                  55                  60

Glu Ser Ser Glu Val Ile Val His Lys Ala Met Asp Ile Glu Tyr Asn
65                  70                  75                  80

Asp Met Phe Asn Asn Phe Thr Val Ser Phe Trp Leu Arg Val Pro Lys
                85                  90                  95

Val Ser Ala Ser His Leu Glu Gln Tyr Gly Thr Asn Glu Tyr Ser Ile
            100                 105                 110

Ile Ser Ser Met Lys Lys His Ser Leu Ser Ile Gly Ser Gly Trp Ser
        115                 120                 125

Val Ser Leu Lys Gly Asn Asn Leu Ile Trp Thr Leu Lys Asp Ser Ala
    130                 135                 140

Gly Glu Val Arg Gln Ile Thr Phe Arg Asp Leu Pro Asp Lys Phe Asn
145                 150                 155                 160

Ala Tyr Leu Ala Asn Lys Trp Val Phe Ile Thr Ile Thr Asn Asp Arg
                165                 170                 175

Leu Ser Ser Ala Asn Leu Tyr Ile Asn Gly Val Leu Met Gly Ser Ala
            180                 185                 190

Glu Ile Thr Gly Leu Gly Ala Ile Arg Glu Asp Asn Asn Ile Thr Leu
        195                 200                 205

Lys Leu Asp Arg Cys Asn Asn Asn Asn Gln Tyr Val Ser Ile Asp Lys
    210                 215                 220

Phe Arg Ile Phe Cys Lys Ala Leu Asn Pro Lys Glu Ile Glu Lys Leu
225                 230                 235                 240

Tyr Thr Ser Tyr Leu Ser Ile Thr Phe Leu Arg Asp Phe Trp Gly Asn
                245                 250                 255

Pro Leu Arg Tyr Asp Thr Glu Tyr Tyr Leu Ile Pro Val Ala Ser Ser
            260                 265                 270

Ser Lys Asp Val Gln Leu Lys Asn Ile Thr Asp Tyr Met Tyr Leu Thr
        275                 280                 285

Asn Ala Pro Ser Tyr Thr Asn Gly Lys Leu Asn Ile Tyr Tyr Arg Arg
    290                 295                 300

Leu Tyr Asn Gly Leu Lys Phe Ile Ile Lys Arg Tyr Thr Pro Asn Asn
305                 310                 315                 320

Glu Ile Asp Ser Phe Val Lys Ser Gly Asp Phe Ile Lys Leu Tyr Val
                325                 330                 335

Ser Tyr Asn Asn Asn Glu His Ile Val Gly Tyr Pro Lys Asp Gly Asn
            340                 345                 350
```

```
Ala Phe Asn Asn Leu Asp Arg Ile Leu Arg Val Gly Tyr Asn Ala Pro
        355                 360                 365

Gly Ile Pro Leu Tyr Lys Lys Met Glu Ala Val Lys Leu Arg Asp Leu
    370                 375                 380

Lys Thr Tyr Ser Val Gln Leu Lys Leu Tyr Asp Asp Lys Asn Ala Ser
385                 390                 395                 400

Leu Gly Leu Val Gly Thr His Asn Gly Gln Ile Gly Asn Asp Pro Asn
                405                 410                 415

Arg Asp Ile Leu Ile Ala Ser Asn Trp Tyr Phe Asn His Leu Lys Asp
            420                 425                 430

Lys Ile Leu Gly Cys Asp Trp Tyr Phe Val Pro Thr Asp Glu Gly Trp
        435                 440                 445

Thr Asn Asp
    450


<210> SEQ ID NO 6
<211> LENGTH: 1359
<212> TYPE: DNA
<213> ORGANISM: Clostridium tetani

<400> SEQUENCE: 6

atgaaaaatc tggattgttg ggttgataat gaagaagata tagatgttat attaaaaaag      60

agtacaattt taaatttaga tattaataat gatattatat cagatatatc tgggtttaat     120

tcatctgtaa taacatatcc agatgctcaa ttggtgcccg gaataaatgg caaagcaata     180

catttagtaa acaatgaatc ttctgaagtt atagtgcata aagctatgga tattgaatat     240

aatgatatgt ttaataattt taccgttagc ttttggttga gggttcctaa agtatctgct     300

agtcatttag aacaatatgg cacaaatgag tattcaataa ttagctctat gaaaaaacat     360

agtctatcaa taggatctgg ttggagtgta tcacttaaag gtaataactt aatatggact     420

ttaaaagatt ccgcgggaga agttagacaa ataactttta gggatttacc tgataaattt     480

aatgcttatt tagcaaataa atgggttttt ataactatta ctaatgatag attatcttct     540

gctaatttgt atataaatgg agtacttatg ggaagtgcag aaattactgg tttaggagct     600

attagagagg ataataatat aacattaaaa ctagatagat gtaataataa taatcaatac     660

gtttctattg ataaatttag gatattttgc aaagcattaa atccaaaaga gattgaaaaa     720

ttatacacaa gttatttatc tataaccttt ttaagagact tctggggaaa cccctttacga     780

tatgatacag aatattattt aataccagta gcttctagtt ctaaagatgt tcaattgaaa     840

aatataacag attatatgta tttgacaaat gcgccatcgt atactaacgg aaaattgaat     900

atatattata gaaggttata taatggacta aaatttatta taaaaagata tacacctaat     960

aatgaaatag attcttttgt taaatcaggt gattttatta aattatatgt atcatataac    1020

aataatgagc acattgtagg ttatccgaaa gatggaaatg cctttaataa tcttgataga    1080

attctaagag taggttataa tgccccaggt atccctcttt ataaaaaaat ggaagcagta    1140

aaattgcgtg atttaaaaac ctattctgta caacttaaat tatatgatga taaaaatgca    1200

tctttaggac tagtaggtac ccataatggt caaataggca acgatccaaa tagggatata    1260

ttaattgcaa gcaactggta ctttaatcat ttaaaagata aaattttagg atgtgattgg    1320

tactttgtac ctacagatga aggatggaca aatgattaa                           1359
```